United States Patent
Winkelman et al.

(10) Patent No.: US 11,490,947 B2
(45) Date of Patent: *Nov. 8, 2022

(54) TATTOO REMOVAL USING A LIQUID-GAS MIXTURE WITH PLASMA GAS BUBBLES

(71) Applicant: Clear Intradermal Technologies, Inc., New York, NY (US)

(72) Inventors: James W. Winkelman, Chestnut Hill, MA (US); Martin E. Schmieg, Marblehead, MA (US)

(73) Assignee: Clear Intradermal Technologies, Inc., New York, NY (US)

( * ) Notice: Subject to any disclaimer, the term of this patent is extended or adjusted under 35 U.S.C. 154(b) by 133 days.

This patent is subject to a terminal disclaimer.

(21) Appl. No.: 16/938,694

(22) Filed: Jul. 24, 2020

(65) Prior Publication Data

US 2020/0352620 A1 Nov. 12, 2020

Related U.S. Application Data

(60) Continuation-in-part of application No. 16/711,549, filed on Dec. 12, 2019, and a continuation-in-part of
(Continued)

(51) Int. Cl.
*A61B 18/14* (2006.01)
*A61B 18/00* (2006.01)
(Continued)

(52) U.S. Cl.
CPC ........ *A61B 18/042* (2013.01); *A61B 18/1477* (2013.01); *A61K 8/19* (2013.01);
(Continued)

(58) Field of Classification Search
CPC ........ A61B 2017/00769; A61B 18/042; A61B 2018/00583; A61B 18/1477;
(Continued)

(56) References Cited

U.S. PATENT DOCUMENTS

| 4,634,420 A | 1/1987 | Spinosa et al. |
| 5,217,455 A | 6/1993 | Tan |

(Continued)

FOREIGN PATENT DOCUMENTS

| DE | 112009000734 T5 | 4/2011 |
| DE | 102011001416 A1 | 9/2012 |

(Continued)

OTHER PUBLICATIONS

Japanese Office Action, JP2018-511363, dated Dec. 22, 2020, 4 pages.
(Continued)

*Primary Examiner* — Joanne M Hoffman
*Assistant Examiner* — Sean W Collins
(74) *Attorney, Agent, or Firm* — Potomac Law Group, PLLC; Reza Mollaaghababa

(57) ABSTRACT

Methods and systems are disclosed for removing a tattoo from a subject's skin by application of a cold plasma that is delivered via a liquid-gas mixture. The plasma can be delivered in the form of gas bubbles, in which at least a portion of gas is in the form of a plasma.

28 Claims, 7 Drawing Sheets

Related U.S. Application Data application No. 16/902,767, filed on Jun. 16, 2020, which is a division of application No. 15/155,750, filed on May 16, 2016, now Pat. No. 10,716,611.

(60) Provisional application No. 62/782,208, filed on Dec. 19, 2018, provisional application No. 62/162,180, filed on May 15, 2015.

(51) Int. Cl.
  *A61B 18/04*    (2006.01)
  *A61K 8/19*     (2006.01)
  *A61K 8/22*     (2006.01)
  *A61Q 1/14*     (2006.01)
  *A61B 17/00*    (2006.01)

(52) U.S. Cl.
  CPC ............... *A61K 8/22* (2013.01); *A61Q 1/145* (2013.01); *A61B 2017/00769* (2013.01); *A61B 2017/00973* (2013.01); *A61B 2018/0016* (2013.01); *A61B 2018/0047* (2013.01); *A61B 2018/00166* (2013.01); *A61B 2018/00196* (2013.01); *A61B 2018/00583* (2013.01); *A61B 2018/00714* (2013.01); *A61B 2018/00916* (2013.01); *A61B 2218/002* (2013.01); *A61B 2218/007* (2013.01)

(58) Field of Classification Search
  CPC .... A61B 2017/00973; A61B 2218/007; A61B 2218/002; A61B 2018/00916; A61B 2018/0047; A61B 2018/0016; A61B 2018/00196; A61Q 1/145; A61K 8/22; A61K 8/19; H05H 1/466
  See application file for complete search history.

(56) References Cited

U.S. PATENT DOCUMENTS

| | | | |
|---|---|---|---|
| 6,053,172 A | 4/2000 | Hovda et al. |
| 6,394,956 B1 | 5/2002 | Chandrasekaran et al. |
| 6,770,070 B1 | 8/2004 | Balbierz |
| 6,896,672 B1 | 5/2005 | Eggers et al. |
| 7,330,755 B2 | 2/2008 | Viol et al. |
| 7,402,435 B2 | 7/2008 | Miyoshi et al. |
| 7,608,839 B2 | 10/2009 | Coulombe et al. |
| 7,633,231 B2 | 12/2009 | Watson |
| 7,683,342 B2 | 3/2010 | Morfill et al. |
| 7,923,251 B2 | 4/2011 | Vankov et al. |
| 8,005,548 A1 | 8/2011 | Watson |
| 8,103,340 A1 | 1/2012 | Viol |
| 8,283,171 A1 | 10/2012 | Vankov et al. |
| 8,377,388 B2 | 2/2013 | Konesky |
| 8,388,618 B2 | 3/2013 | Fridman et al. |
| 8,455,228 B2 | 6/2013 | Jaroszeski et al. |
| 8,460,283 B1 | 6/2013 | Laroussi et al. |
| 8,521,274 B2 | 8/2013 | Gutsol et al. |
| 8,557,187 B2 | 10/2013 | Ehlbeck et al. |
| 8,725,248 B2 | 5/2014 | Gutsol et al. |
| 8,802,022 B2 | 8/2014 | Konesky |
| 8,810,134 B2 | 8/2014 | Watson |
| 8,828,326 B2 | 9/2014 | Holbeche |
| 8,894,644 B2 | 11/2014 | Stieber et al. |
| 8,900,521 B2 | 12/2014 | Hancock |
| 8,906,659 B2 | 12/2014 | Clyne et al. |
| 8,926,920 B2 | 1/2015 | Morfill et al. |
| 8,928,230 B2 | 1/2015 | Watson et al. |
| 8,957,572 B2 | 2/2015 | Eden et al. |
| 8,992,518 B2 | 3/2015 | Fridman et al. |
| 8,994,271 B2 | 3/2015 | Kindel et al. |
| 9,005,188 B2 | 4/2015 | Wandke et al. |
| 9,006,976 B2 | 4/2015 | Watson et al. |
| 9,038,645 B2 | 5/2015 | Wandke et al. |
| 9,072,157 B2 | 6/2015 | Holbeche et al. |
| 9,192,776 B2 | 11/2015 | Hummel et al. |
| 9,226,790 B2 | 1/2016 | Zemel et al. |
| 9,236,227 B2 | 1/2016 | Watson et al. |
| 9,257,264 B2 | 2/2016 | Hummel et al. |
| 9,287,094 B2 | 3/2016 | Trutwig et al. |
| 9,295,535 B2 | 3/2016 | Holbeche et al. |
| 9,308,285 B2 | 4/2016 | Hancock et al. |
| 9,330,890 B2 | 5/2016 | Busse et al. |
| 9,339,783 B2 | 5/2016 | Fridman et al. |
| 9,345,120 B2 | 5/2016 | Wandke et al. |
| 9,351,790 B2 | 5/2016 | Zemel et al. |
| 9,384,947 B2 | 7/2016 | Watson et al. |
| 9,387,369 B2 | 7/2016 | Yamamoto |
| 9,418,820 B2 | 8/2016 | Watson et al. |
| 9,437,401 B2 | 9/2016 | Watson et al. |
| 9,440,057 B2 | 9/2016 | Jacofsky et al. |
| 9,472,382 B2 | 10/2016 | Jacofsky |
| 9,498,637 B2 | 11/2016 | Sanders et al. |
| 9,511,240 B2 | 12/2016 | Dobrynin et al. |
| 9,521,736 B2 | 12/2016 | Jacofsky et al. |
| 9,538,630 B2 | 1/2017 | Watson |
| 9,558,918 B2 | 1/2017 | Watson et al. |
| 9,570,273 B2 | 2/2017 | Watson et al. |
| 9,601,317 B2 | 3/2017 | Konesky |
| 2001/0029373 A1 | 10/2001 | Baker et al. |
| 2003/0125727 A1* | 7/2003 | Truckai ............... A61B 18/042 606/41 |
| 2006/0058238 A1 | 3/2006 | Laurent-Applegate et al. |
| 2007/0027446 A1 | 2/2007 | Goble |
| 2007/0078448 A1 | 4/2007 | Lipman |
| 2008/0221548 A1 | 9/2008 | Danenberg et al. |
| 2009/0112205 A1 | 4/2009 | McGill et al. |
| 2010/0107744 A1 | 5/2010 | Fukuda et al. |
| 2010/0228182 A1* | 9/2010 | Clark, III ......... A61B 17/32093 606/171 |
| 2010/0247687 A1 | 9/2010 | Arnold-Ronish |
| 2010/0249768 A1 | 9/2010 | Avramenko |
| 2010/0262135 A1 | 10/2010 | Berube |
| 2011/0022043 A1 | 1/2011 | Wandke et al. |
| 2011/0171188 A1 | 7/2011 | Morfill et al. |
| 2011/0301412 A1 | 12/2011 | Cho |
| 2012/0046597 A1 | 2/2012 | Morfill et al. |
| 2012/0046602 A1 | 2/2012 | Morfill et al. |
| 2012/0046658 A1 | 2/2012 | Kreindel |
| 2012/0064016 A1 | 3/2012 | Lloyd et al. |
| 2012/0080412 A1 | 4/2012 | Holbeche et al. |
| 2012/0107761 A1 | 5/2012 | Holbeche et al. |
| 2012/0107896 A1 | 5/2012 | Wandke et al. |
| 2012/0288934 A1 | 11/2012 | Weltmann et al. |
| 2013/0026137 A1 | 1/2013 | Kindel et al. |
| 2013/0040542 A1 | 2/2013 | Schwappach et al. |
| 2013/0147340 A1 | 6/2013 | Holbeche |
| 2013/0345620 A1 | 12/2013 | Zemel et al. |
| 2014/0188037 A1 | 7/2014 | Jacofsky et al. |
| 2014/0188071 A1 | 7/2014 | Jacofsky et al. |
| 2014/0188097 A1 | 7/2014 | Watson et al. |
| 2014/0188195 A1 | 7/2014 | Jacofsky et al. |
| 2014/0200506 A1 | 7/2014 | Zemel et al. |
| 2014/0207053 A1 | 7/2014 | Morfill et al. |
| 2014/0257276 A1* | 9/2014 | Sartor ............... A61B 18/042 606/41 |
| 2014/0341786 A1 | 11/2014 | Konesky |
| 2014/0378892 A1 | 12/2014 | Keidar et al. |
| 2015/0004248 A1 | 1/2015 | Morfill et al. |
| 2015/0071099 A1 | 3/2015 | Yi et al. |
| 2015/0088234 A1 | 3/2015 | Weltmann et al. |
| 2015/0094647 A1 | 4/2015 | Kalghatgi et al. |
| 2015/0112300 A1 | 4/2015 | Glowacki et al. |
| 2015/0123711 A1 | 5/2015 | Mandela et al. |
| 2015/0151135 A1 | 6/2015 | Kalghatgi et al. |
| 2015/0157870 A1 | 6/2015 | Kalghatgi et al. |
| 2015/0209595 A1 | 7/2015 | Kalghatgi et al. |
| 2015/0340207 A1 | 11/2015 | Holbeche |
| 2016/0045246 A1 | 2/2016 | Stieber et al. |
| 2016/0089545 A1 | 3/2016 | Juluri et al. |
| 2016/0100853 A1 | 4/2016 | Hyde et al. |
| 2016/0106993 A1 | 4/2016 | Watson et al. |
| 2016/0113701 A1 | 4/2016 | Zemel et al. |
| 2016/0121134 A1 | 5/2016 | Kalghatgi et al. |

(56) References Cited

U.S. PATENT DOCUMENTS

| | | |
|---|---|---|
| 2016/0166818 A1 | 6/2016 | Kalghatgi et al. |
| 2016/0192961 A1 | 7/2016 | Ginggen et al. |
| 2016/0220670 A1 | 8/2016 | Kalghatgi et al. |
| 2016/0236002 A1 | 8/2016 | Dirk et al. |
| 2016/0242269 A1 | 8/2016 | Dirk et al. |
| 2016/0271411 A1 | 9/2016 | Hummel et al. |
| 2016/0271412 A1 | 9/2016 | Hummel et al. |
| 2016/0331436 A1 | 11/2016 | Holbeche |
| 2016/0331437 A1 | 11/2016 | Holbeche et al. |
| 2016/0331439 A1 | 11/2016 | Winkelman et al. |
| 2016/0331989 A1 | 11/2016 | Cho et al. |
| 2016/0338184 A1 | 11/2016 | Holbeche |
| 2016/0338755 A1 | 11/2016 | Holbeche et al. |
| 2016/0354614 A1 | 12/2016 | Watson et al. |
| 2016/0361558 A1 | 12/2016 | Jacofsky et al. |
| 2017/0246440 A1 | 8/2017 | Kalghatgi et al. |
| 2017/0246468 A1 | 8/2017 | Kalghatgi et al. |
| 2017/0326347 A1 | 11/2017 | Kalghatgi et al. |
| 2018/0103991 A1 | 4/2018 | Linhart et al. |
| 2018/0130646 A1 | 5/2018 | Louis |
| 2018/0311079 A1 | 11/2018 | Garibyan et al. |
| 2020/0197077 A1 | 6/2020 | Winkelman et al. |
| 2020/0197078 A1 | 6/2020 | Winkelman et al. |
| 2020/0305950 A1 | 10/2020 | Winkelman et al. |

FOREIGN PATENT DOCUMENTS

| | | |
|---|---|---|
| DE | 102013107448 B4 | 11/2016 |
| EP | 1638469 A2 | 3/2006 |
| EP | 1670369 A1 | 6/2006 |
| EP | 2016809 A2 | 1/2009 |
| EP | 1810626 B1 | 1/2012 |
| EP | 3051926 A1 | 8/2016 |
| JP | 2009507773 A | 2/2009 |
| JP | 2014212839 A | 11/2014 |
| JP | 6208968 B2 | 10/2017 |
| KR | 20150142162 A | 12/2015 |
| KR | 1020160121809 A | 10/2016 |
| RU | 2727147 C1 | 7/2020 |
| WO | 2001050963 A1 | 7/2001 |
| WO | 2003096767 A1 | 11/2003 |
| WO | 2007015232 A1 | 2/2007 |
| WO | 2010107746 A1 | 9/2010 |
| WO | 2011/055368 A2 | 5/2011 |
| WO | 2011058301 A1 | 5/2011 |
| WO | 2011128620 A1 | 10/2011 |
| WO | 2012106735 A2 | 8/2012 |
| WO | 2012167089 A1 | 12/2012 |
| WO | 2014020584 A1 | 2/2014 |
| WO | 2015021434 A2 | 2/2015 |
| WO | 2016020407 A1 | 2/2016 |
| WO | 2016037599 A1 | 3/2016 |
| WO | 2016079742 A1 | 5/2016 |
| WO | 2016128873 A1 | 8/2016 |
| WO | 2016187132 A1 | 11/2016 |
| WO | 2016192986 A1 | 12/2016 |
| WO | 2016192997 A1 | 12/2016 |
| WO | 2017008781 A1 | 1/2017 |
| WO | 2017021585 A1 | 2/2017 |
| WO | 2020131544 A1 | 6/2020 |
| WO | 2020131545 A1 | 6/2020 |

OTHER PUBLICATIONS

International Preliminary Report on Patentability, PCT/US2019/065873, dated Jul. 1, 2021, 9 Pages.

International Preliminary Report on Patentability, PCT/US2019/065876, dated Jul. 1, 2021, 10 Pages.

Australin Examination Report, AU2016263428, dated Sep. 4, 2020, 5 pages.

International Search Report and Written Opinion, PCT/US2021/042267 dated Oct. 29, 2021, 13 pages.

Choi, J-H et al., "Treatment with low-temperature atmospheric pressure plasma enhances cutaneous delivery of Epidermal growth factor by regulating E-cadherin-mediacted cell junctions," Arch Dermatol., vol. 306:635-643 (2014).

Colver, et al. " Tattoo Removal Using a Liquid Nitrogen Cryospray" Clinical and Experimental Dermatology, vol. 9, No. 1, Jul. 1, 1984, pp. 364-366.

Gucker, Plasma Discharges in Gas Bubbles in Liquid Water: Breakdown Mechanisms and Resultant Chemistry Ph.D. Thesis, University of Michigan (2015), 2 Pages.

Hamon, et al. Characterization of Plasma Generation in Bubbles With a Plasma Gun. 22nd International, 1 Page.

International Search Report and Written Opinion, PCT/US2016/032731, dated Aug. 1, 2016, 9 pages.

International Search Report and Written Opinion, PCT/US2017/019259 dated May 31, 2017, 14 pages.

International Search Report and Written Opinion, PCT/US2019/065873, dated Apr. 17, 2020, 15 pages.

International Search Report and Written Opinion, PCT/US2019/065876, dated Apr. 6, 2020, 16 pages.

Japanese Office Action, JP2018-511363, dated Mar. 17. 2020, 3 pages.

Sommers et al. Plasma Formation in Underwater Bubbles, Plasma Sources Science and Technology, vol. 23, No. 1 (2014), 5 Pages.

Japanese Office Action for Japanese Application No. 2021-071986, dated Mar. 8, 2022.

Mexican First Office Action, MX/a/2020/013395, dated Mar. 10, 2022, 4 pages.

Huzaira M et al., "Magnetic Tattoos", Lasers in Surgery and Medicine, New York, NY, US, vol. 31, No. 2, Aug. 1, 2002 (Aug. 1, 2002), pp. 121-128.

International Search Report and Written Opinion, PCT/US2021/058746, dated Feb. 23, 2022, 16 pages.

* cited by examiner

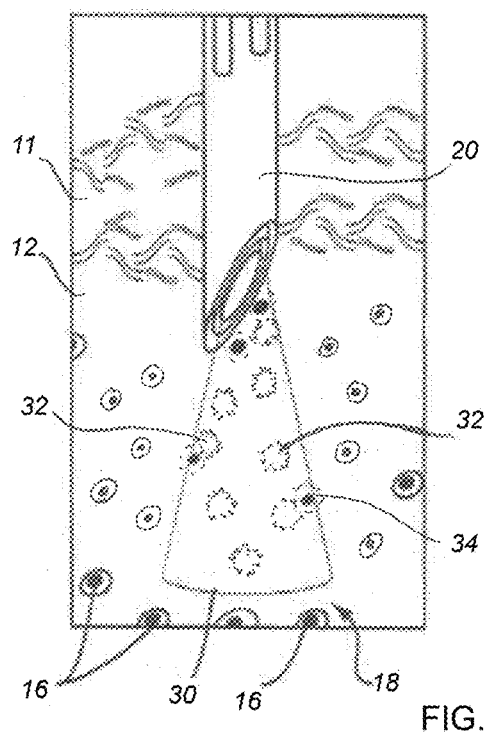
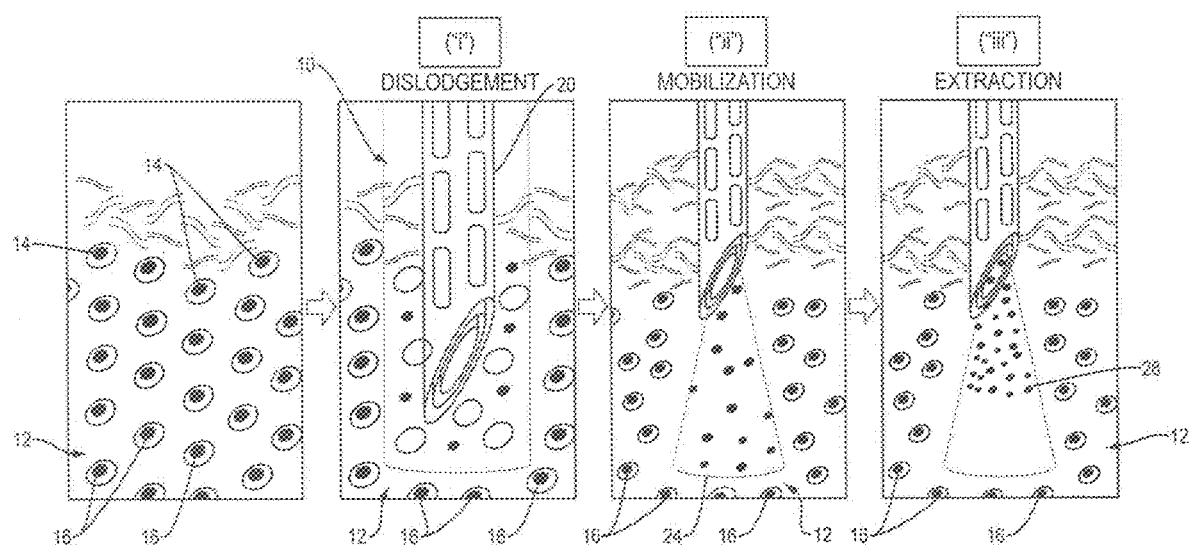
FIG. 1A    FIG. 1B    FIG. 1C    FIG. 1D

FRONT VIEW

SIDE VIEW

FRONT VIEW

SIDE VIEW

FRONT VIEW

SIDE VIEW

TATTOO REMOVAL USING A LIQUID-GAS MIXTURE WITH PLASMA GAS BUBBLES

CROSS-REFERENCE TO RELATED APPLICATIONS

This application is a continuation-in-part of U.S. patent application Ser. No. 16/711,549 filed Dec. 12, 2019, which claims priority to, and the benefit of U.S. Provisional Application No. 62/782,208, filed on Dec. 19, 2018, the entire teachings of which are incorporated herein by reference.

This application is also a continuation-in-part of U.S. patent application Ser. No. 16/902,767 filed on Jun. 16, 2020, which is division of U.S. patent application Ser. No. 15/155,750 filed May 16, 2016, now U.S. Pat. No. 10,716,611, which claims priority to, and the benefit of U.S. Provisional Application No. 62/162,180, filed on May 15, 2015, the entire teachings of which are also incorporated herein by reference.

FIELD

The present invention relates to methods and systems of skin treatment and, in particular, tattoo removal, by applying a cold atmospheric plasma.

BACKGROUND

Permanent tattoos are created by piercing the skin with needles or similar instruments to mechanically deliver an ink, which includes small particles of pigments/dyes suspended in a carrier, into the dermal layer of the skin. The creation of a permanent tattoo requires the insertion/implantation of pigments, dyes, and/or chromophores into the dermis which are not dissolvable and/or biodegradable. Following mechanical insertion of the ink particles and during the healing process, the majority of the ink particles that remain in the dermis and that have not otherwise been expelled from the skin or absorbed by the body in the healing process, 70-80%, are engulfed by phagocytic skin cells (such as fibroblasts and macrophages) or retained in the extracellular matrix of the dermis and the remaining ink particles are found such that 10-15% of the ink particles lie flattened on collagen fibers and 5-10% of the ink particles lie attached on the serosal side of capillaries.

Despite the wide acceptance and popularity of permanent tattoos, there is a significant demand for the removal of tattoos. Removal of tattoos, however, represents a complex process that most typically involves the use of lasers designed for aesthetic skin treatments and/or other mechanical removal techniques. The current state-of-the-art for tattoo removal is performed using a variety of lasers which induce degradation and absorption by the body of the inks to achieve tattoo removal. The laser conditions require matching the laser frequencies to the particles according to their size, composition, color, and depth in the dermis. The laser is applied to the tattoo such that the pigments, dyes, and/or chromophores of the ink particles absorb the laser light and the laser pulses dissociate and degrade the pigments, dyes, and/or chromophores components of the ink particles into small(er) fragments. The fragmented ink components may become small enough to be absorbed by the body and removed from the dermis. Nonetheless, laser-based removal of tattoos has several shortcomings. For example, lasers induce heating of the skin and can cause burns as well as other undesirable tissue damage which can cause some scarring or color variations that are likely to remain after healing. Current laser-based procedures for tattoo removal may therefore be somewhat ineffective at complete removal of tattoo inks, require multiple treatments at a high cost, cause pain, and can result in scarring, disfigurement, and depigmentation of the treated skin.

Therefore, it would be advantageous to provide a system and methods for tattoo removal using non-laser-based approaches. It would also be advantageous to provide methods that enable removal/extraction of the degraded ink components, such as dyes, pigments and other chromophores, from the body to reduce absorption by the body of potentially harmful/toxic chemicals.

It is therefore an object of the present teachings to provide a system and method for removing a tattoo from a subject by degrading ink particles trapped within the dermis.

It is an additional object of the present teachings to provide such a system and method which allows for the extraction of the residue of treated tattoo ink particles, which may have toxic properties, and of other degradation components from the subject's skin tissues.

It is yet another object of the present teachings to provide methods for removing tattoos which can be performed in one or more treatments and which are effectively less painful to the subject being treated than current conventional methods of tattoo removal.

It is still a further object of the present teachings to provide methods of tattoo removal which can address the limitations of current state-of-the-art removal methods (i.e., laser-based removal systems) to reduce issues with skin scarring, skin color bleaching, and residual tattoo shadowing remaining after removal treatment(s).

SUMMARY

Methods and systems are disclosed for removing a tattoo from a subject's skin by application of a cold plasma that is delivered via a liquid-gas mixture. The plasma can be delivered in the form of gas bubbles, in which at least a portion of gas is in the form of a plasma.

In one aspect of the invention, methods of removing a tattoo from a subject's skin are disclosed comprising the steps of: (i) forming an activated liquid-gas mixture comprising a liquid with plasma gas bubbles; (ii) delivering the activated liquid-gas mixture to a target tattoo region within a dermal region of the skin; whereby tattoo ink particles can be dislodged by the application of said plasma to the target tattoo region.

The step of forming an activated liquid-gas mixture can further comprise activating a liquid with entrained gas bubbles by applying a high energy electric field to the liquid to induce plasma formation in the gas bubbles. Alternatively, the step of forming an activated liquid-gas mixture can further comprise applying a high energy electrical field to a gas to form a gas plasma and then mixing the gas plasma with a liquid to form the activated liquid gas mixture.

In certain embodiments, the plasma gas bubbles comprise a cold atmospheric plasma, wherein the plasma gas bubbles apply energy to the target tattoo region without raising the temperature of the target region more than 4 degrees C. The plasma gas bubbles can further comprise at least one gas selected from air, carbon oxide, oxygen, nitrogen, helium, argon, neon, xenon, and krypton. The liquid component of the activated liquid-gas mixture can comprises at least one liquid selected from water, saline, and buffered aqueous solutions. In certain embodiments, the liquid-gas mixture can comprise water with dissolved carbon dioxide. The liquid component can also comprise one or more surfactants, local anesthetics, anti-infective agents, antiseptic agents, anti-inflammatory agents, or combinations thereof.

The activated liquid-gas mixture, sometimes referred to herein as fluid cold atmospheric plasma (F-CAP) can also be applied in conjunction with a gas-only cold atmospheric plasma (CAP). For example, the target tattoo region can be treated first by a CAP treatment, then by F-CAP, or vice-versa. Between CAP and F-CAP treatment, one or more additional mobilization or extraction steps can be practiced. For further details on CAP treatment, see commonly owned U.S. Pat. No. 10,716,611, herein incorporated by reference in its entirety.

In addition to conveying the plasma gas bubbles to the target tattoo region of the dermis, the liquid component of the activated liquid-gas mixture can serve as a mobilization fluid such treatment of tattoo-containing cellular structures and mobilization of dislodged tattoo ink particles occurs concurrently. Alternatively, the methods of the present invention can include the step of pretreating the target tattoo region by injecting the region with a separate mobilization fluid. For example, injections of a fluid such distilled water or saline can be delivered to the target tattoo region prior to plasma treatment. A series of blebs can be formed in the skin by such injections, which can assist in registration of the treatment apparatus and/or permit outgassing of gas during or following treatment. The pretreatment mobilization fluid that remains in the dermis can also facilitate extraction of dislodged or degraded ink particles following treatment.

The step of delivering the activated liquid-gas mixture to a target tattoo region can further comprise accessing the target tattoo region via at least one hollow needle inserted into the subject's skin. In some embodiments, multiple needles can be used to deliver the active liquid gas mixture. The liquid-gas mixture can be formed prior to plasma generation, during plasma generation or following plasma generation. For example a concentric dual lumen tubular plasma generator can include separate passageways for the liquid (e.g., in an inner lumen) and the gas that will be ignited into a plasma (e.g., in an outer lumen). The liquid and plasma can be mixed in the plasma generator, or at the entry into a delivery needle or other treatment applicator or even in the dermis.

The method can further comprise applying suction to the target region, either via a separate device or via the treatment component. For example, dual lumen needles can again be employed with one lumen utilized to deliver the activated liquid-gas mixture and another lumen utilized to extract dislodged or degraded ink particles via suction. Extraction of the ink particles can be achieved via suction of a mobilization fluid and/or suction of a natural bodily fluid containing the particles from the target region.

The step of forming an active liquid-gas mixture can further comprise igniting a plasma in the gas component by a high strength electric field so that gas atoms are stripped of at least some of their orbital electrons. In certain embodiments, the plasma can be initiated by applying an alternating electric field having at least one frequency ranging from about 1 kHz to 100 MHz. The plasma initiation step can further comprise delivering between about 0.1 and 10 microamperes, or between about 1 and 10 microamperes, of alternating current. The plasma initiation step can also comprise applying a DC voltage between about 1 and 10 kV, or between about 4 and 6 kV.

The method of the present invention can further comprise delivering a separate mobilization fluid to the target region before, during or after delivering the activated liquid-gas mixture to a target tattoo region. This mobilization fluid comprises at least one of sterile water, a saline solution, or a buffered aqueous solution and optionally one or more surfactants, local anesthetics, anti-infective agents, antiseptic agents, anti-inflammatory agents, or combinations thereof.

In another aspect of the invention, A system for removing a tattoo from a subject's skin, the system comprising: (i) a gas source; (ii) a liquid source; a plasma generator for generating an activated liquid-gas mixture comprising a liquid with plasma gas bubbles; and a conduit for delivery of the activated liquid-gas mixture to target tattoo region.

The system can further comprise a mobilization fluid delivery component for delivering a liquid either from the liquid source or from an alternative liquid source to the target tattoo region either before, during or after delivery of the activated liquid-gas mixture. In one embodiment, the system can further comprise a syringe and needle to deliver of the mobilization fluid.

The system can also comprise an extraction component. In certain embodiments, the extraction component applies suction to the subject's tattooed dermis during or after the application of the activated liquid-gas mixture with plasma gas bubbles.

The system can also include a treatment applicator configured to pierce skin and deliver the activated liquid-gas mixture to a tattoo region in a subject's dermis. For example, the treatment applicator can be a hollow needle with a tip, from which the activated liquid-gas mixture is applied to the target tattoo region. The hollow needle can be an single lumen needle or a multi-lumen, e.g., a multiple sheathed, needle The treatment system can also include an array of needles, each capable of delivering the activated liquid-gas mixture to the target tattoo region. The treatment applicator comprises a removable, replaceable and/or disposable cartridge with one or more needles configured to penetrate the subject's tattooed skin.

In certain embodiments, the treatment applicator further comprises a kinetic actuator that induces movement of the treatment applicator during treatment. For example, the kinetic actuator can cause an active tip of the applicator to penetrate and at least partially withdraw from the target region or to laterally vibrate within the target region, e.g., at a rate from about 0.01 Hz to 10 kHz, more preferably from about 0.1 Hz to about 1 kHz, or at a rate of at least 10 times per minute.

The methods and systems of the invention apply energy in the form of a cold plasma at a strength and duration to chemically degrade tattoo ink particles. The applied energy can also rupture cell membranes of tattoo ink-bearing macrophages in the dermis and/or disrupt the extracellular dermal matrix to release tattoo ink particles entrapped within the cells or extracellular matrix.

The plasma generator can be connected to a power supply, operating under the control of a controller to deliver electrical energy capable of igniting a plasma in at least some of the gas atoms or molecules. The plasma can be formed by applying an alternating electric field having at least one frequency ranging from about 1 kHz to 100 MHz. For example, the active electrode can deliver between about 0.1 and 10 microamperes, optionally between about 1 and 10 microamperes of alternating current and/or a voltage between about 1 and 10 kV, optionally between about 4 and 6 kV.

Alternatively or in addition, the power supply can supply electrical energy to the plasma generator as a DC voltage. In certain embodiments, the power supply can deliver an pulsed DC current having a pulse repetition rate ranging from about 1 kHz to 100 MHz. For example, an active electrode connected to the power supply can deliver DC pulses at between about 0.1 and 10 microamperes, optionally between about 0.1 and 1 microamperes and/or at a voltage between about 1 and 10 kV, optionally between about 4 and 6 kV.

The plasma can be delivered without raising the temperature of the target region more than 4 degrees C.

The methods of the present invention preferably also includes the steps of mobilizing and extracting dislodged or degraded ink particles. For example, the step of mobilizing ink particles can further comprise delivering a mobilization fluid to the target region. The mobilization fluid can include at least one of sterile water, a saline solution, or a buffered aqueous solution as well as one or more surfactants, local anesthetics, anti-infective agents, antiseptic agents, anti-inflammatory agents, or combinations thereof. The extraction step can include extracting ink particles via suction of a mobilization fluid or a natural bodily fluid containing the particles from the target region.

Systems according to the invention can further include an extraction component and optionally a fluid delivery component. The system can further comprise a treatment applicator (e.g., a handpiece), which can include at least one fluid passageway for fluid delivery and/or extraction. The extraction component can apply suction to the subject's tattooed dermis during and/or subsequent to application of the plasma gas bubbles.

In some embodiments, the treatment applicator, the fluid delivery component, the extraction component are integrated into a single treatment component. The treatment component can be in the form of a hollow needle with a tip, from which the activated liquid-gas mixture is applied to the target tattoo region. The hollow needle can be a multiple sheathed needle and, in certain embodiments, the treatment component can comprises a cartridge unit with one or more needles which penetrate the subject's tattooed skin. The cartridge unit can removable, replaceable, and/or disposable.

In some embodiments, cold plasma in the form of gas bubbles within a liquid delivery vehicle is applied via the treatment component to the tattooed dermis and surrounding tissue under the control of a skilled/trained operator or technician and the treatment is applied with a high level of precision. In certain embodiments, all or a portion of the tattoo ink particles are dislodged or degraded, and extracted from the subject's tattooed dermis, to render the tattoo undetectable, invisible, and/or non-discernible to the naked eye.

Methods and systems using applied plasma to remove tattoos from a subject have been developed based on application of an alternating current (AC) or a pulsed direct current (DC) electric field to form a gas plasma which can dislodge and degrade tattoo ink particles trapped within a subject's dermis to facilitate the removal of the mobilized ink particles and/or degradation products thereof from the subject's dermis and surrounding tissues and render the tattoo invisible, non-discernible, and/or undetectable.

The plasma gas bubbles can be applied at a fluence and duration sufficient to chemically degrade tattoo ink particles, or at a fluence and duration to sufficient disrupt the extracellular dermal matrix, or at a fluence and duration sufficient to rupture cell membranes of tattoo ink-bearing macrophages and release tattoo ink particles entrapped therein.

Preferably, the plasma is applied without raising the temperature of the target region more than 4 degrees C. The plasma can also be applied in conjunction with electrical energy.

In certain embodiments, the method can further include the steps of mobilizing and extracting dislodged or degraded ink particles. For example, degraded ink particles can be mobilized by delivering a mobilization fluid to the target region. The mobilization fluid can include at least one of sterile water, a saline solution, or a buffered aqueous solution, and optionally can further include one or more surfactants, or one or more local anesthetics, anti-infective agents, antiseptic agents, anti-inflammatory agents, or combinations thereof.

The extraction step can include extracting degraded ink particles via suction of a mobilization fluid or a natural bodily fluid containing the particles from the target region. The method can also repeat the mobilizing and extracting steps, or cycle the plasma application, mobilization and extraction steps. The treatment applicator and/or mobilization and extraction elements can also be in motion during operation, e.g., vibrating or oscillating in depth, to further augment their function and/or expose a larger portion of the target region.

In certain embodiments, the system can also employ a plurality of electrodes disposed in an array with the electrodes separated from each other by a distance sufficient to achieve a generally uniform electric field over at least a portion of target region by overlapping fields. In some embodiments, the electrode array can include multiple electrodes arranged in rows and/or columns, for example, at least 9 active electrodes, or optionally at least 16 electrodes, or optionally at least 24 electrodes, arranged in a honeycomb pattern. The electrodes can augment the application of F-CAP by providing additional energy to the target tattoo region.

The systems of the present invention can also include an extraction component and optionally a fluid delivery component. When an extraction component is utilized in the system, the extraction component can provide suction or apply suction to the subject's tattooed dermis during and/or subsequent to application of the F-CAP.

The plasma generator, the fluid delivery component, and the extraction component can integrated into a treatment probe having at least one hollow needle with a tip, from which the plasma gas bubbles are applied to the target tattoo region. At least one lumen within the probe can provide mobilization fluid and/or suction to the target tattoo region. The hollow needle can further include a multiple sheathed needle, e.g., with coaxial parallel lumens or concentric lumens to separate the mobilization and extraction conduits.

The treatment component can take the form of a cartridge that can be coupled to a reusable hand piece. For example, the cartridge can include a plurality of needles which penetrate the subject's tattooed skin. The cartridge unit can be removable, replaceable, and/or disposable.

Additionally, the system can further include a mechanical actuator oscillator connected to the one or more active electrodes to permit movement during operation, e.g., vibratory or oscillatory movement of the electrode during treatment.

In one preferred embodiment, F-CAP is applied to the subject's dermis via one or more needles or probe-like structures that penetrate the subject's tattooed skin. The plasma gas bubbles can be applied so that the energy interacts with constituents present within the dermis such as, but not limited to, the tattoo ink particles themselves, macrophages, fibroblasts, cell membranes, collagen fibers, and capillaries and other cellular and non-cellular constituents of the dermis which have trapped the tattoo ink particles in such a manner as to effectively disrupt the tissue components and dislodge the trapped tattoo ink particles. The plasma gas bubbles may also induce degradation of certain types of the ink particles, which are composed of organic and/or inorganic pigments, dyes, and/or chromophores and give color to the ink particles. In preferred embodiments, the electrical energy both degrades and dislodges the trapped ink particles without causing any damage or any significant amount of thermal or other type of irreparable damage to the exposed dermis or other surrounding tissue.

In some embodiments, the cold plasma effectively dislodges and/or degrades all or a portion of the tattoo ink particles during a single or multiple tattoo removal treatment. Multiple treatments may be applied wherein the number of treatments depends on factors such as the size and complexity of the tattoo and on the health of the individual and/or individual's skin. As noted above F-CAP and CAP can be applied sequentially together.

In some embodiments, the dislodged ink particles and degradation by-products thereof can be mobilized to remove them from the subject's dermis and surrounding tissues prior to their recapture by the natural protection mechanisms of the skin, which can otherwise result in a shadowing effect or prior to their transport through the lymphatic channels and deposition in lymph nodes.

In some embodiments, the mobilization step involves the delivery of a pharmaceutically acceptable mobilization fluid which facilitates the removal of the dislodged and degraded ink particles and by-products thereof. The mobilization fluid delivered to the treated dermis is extracted in a subsequent extraction step such as by the application of suction. The extraction of the mobilization fluid containing the dislodged and degraded ink particles from the dermis and surrounding tissues removes the tattoo from the skin.

All or a portion of the dislodged and degraded tattoo ink particles and by-products thereof can be extracted from the subject's tattooed dermis during an extraction step. By degrading, dislodging and removing the tattoo ink particles, the tattoo on skin treated according to the method described herein becomes undetectable, invisible, and/or non-discernible to the naked eye. In certain other embodiments, the cold plasma can degrade all or a portion of the tattoo ink particles and the degradation by-products are converted into colorless components and the tattoo becomes undetectable, invisible, and/or non-discernible to the naked eye. In such embodiments, treatment of the tattoo ink particles with applied plasma gas bubbles may render the ink particles down to their colorless atomic, molecular, and/or gaseous components, such as carbon dioxide or water. In some embodiments, the colorless components may not need to be removed or otherwise extracted from the skin if the tattoo has otherwise been rendered undetectable, invisible, and/or non-discernible to the naked eye. In other embodiments, the dislodged and degraded ink particles and degradation by-products thereof which are rendered into colorless components may be absorbed by natural processes from the interstitial fluid of the dermis or elsewhere in the body.

The extraction of the degraded and dislodged ink particles and by-products thereof from the subject's skin is advantageous as the ink particles, components and degradation by-products thereof may have toxic properties which can potentially have harmful effects if absorbed by the subject's body.

In another embodiment, a system for removal of tattoos using applied electrical energy is formed of (1) an F-CAP generation component; (2) an optional auxiliary fluid delivery component; and (3) a fluid extraction component. The F-CAP component is coupled and connected to a treatment component for delivery of the electrical energy to the tattooed dermis of a subject. The fluid delivery component of the system delivers mobilization fluid to the treatment component which in turn is used to deliver the fluid to the tattooed dermis and surrounding tissue. The mobilization fluid is formed of a pharmaceutically acceptable formulation and facilitates the removal of dislodged and degraded tattoo ink particles and degradation by-products thereof and tissue degradation by-products formed or created during or after exposure to the electrical energy.

The fluid extraction component of the system can be coupled and connected to the treatment component to provide suction for extraction of the mobilization fluid and/or removal/extraction of dislodged and degraded tattoo ink particles which may be present in the natural fluids present in the dermis or surrounding tissue directly.

In some embodiments of the system, the F-CAP component, an optional kinetic applicator, fluid delivery component, and a fluid extraction component may be incorporated into a combined free-standing treatment instrument or system. In some embodiments, the fluid delivery and/or extraction components can be excluded from the combined treatment instrument.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

FIG. 1 is a schematic illustration of tattoo removal by cold plasma using a liquid with entrained gas according to the invention.

FIGS. 1A-1D shows a non-limiting example of one method for tattoo removal according to invention. FIG. 1A show a tattoo in which ink particles are entrapped within dermal tissue structures. FIG. 1B the steps of dislodgement of intra-cellularly trapped tattoo ink particles with a cold atmospheric plasma, mobilization of the dislodged and degraded ink particles, and extraction of the ink particles for removal of a tattoo from a subject's dermis and surrounding tissue.

FIG. 7A illustrates a two electrode array and the respective electric fields when electrical energy is applied to the individual electrodes. FIG. 7B is a graph of electrical field intensity versus distance from each electrode and further illustrating (by a dotted line) to increased field uniformity due to the overlapping fields. FIG. 7C illustrates a multi-electrode array with electrodes in a "honeycomb" arrangement to further enhance field uniformity.

Figure 2:
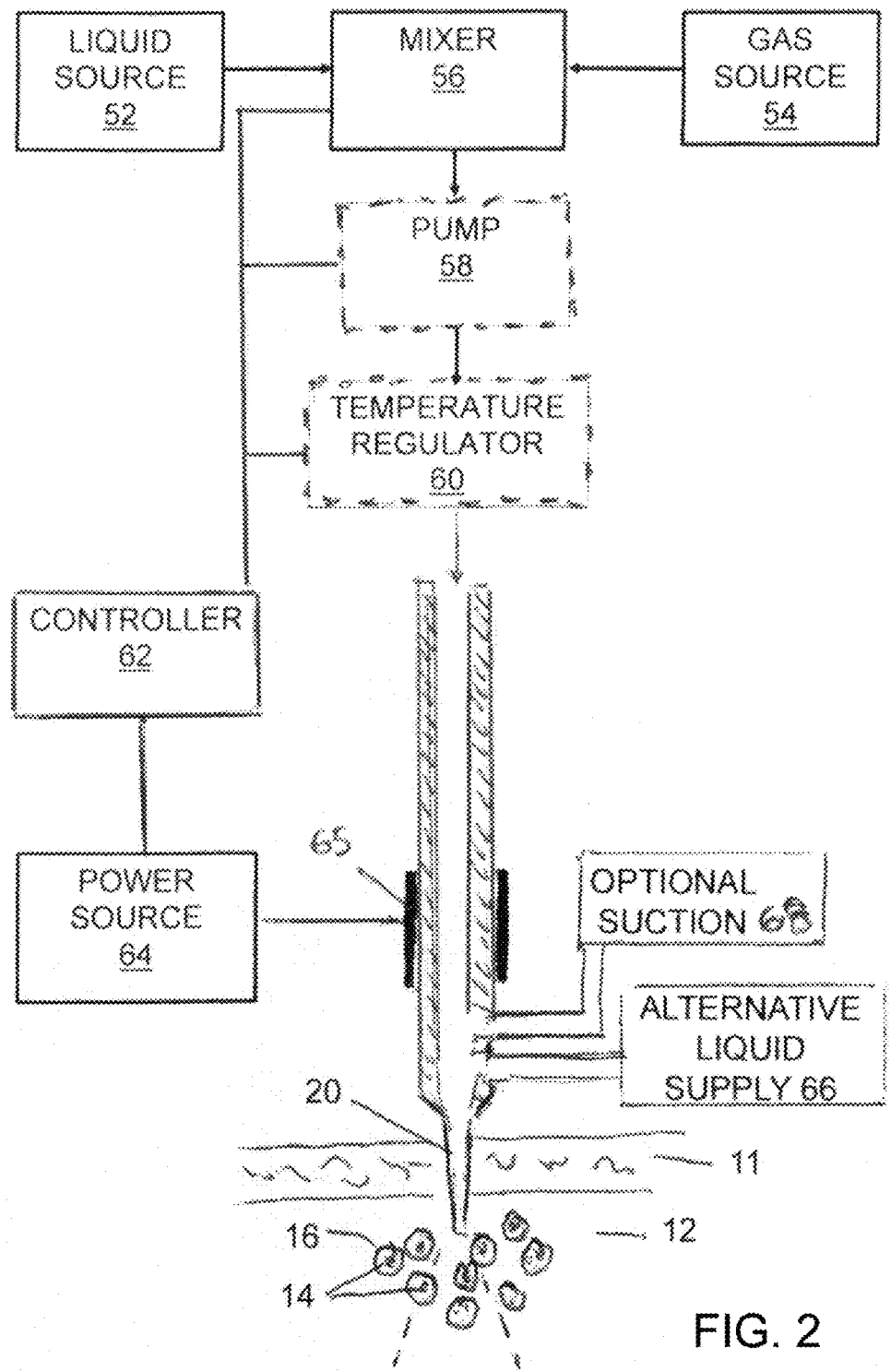
FIG. 2 is a schematic illustration of a tattoo removal system capable of applying an activated liquid-gas mixture to a target tattoo region.

It should be understood that a number of modifications can be made to the system and/or components shown in the Figures. For the purposes of clarity, not every component is labeled in every illustration of the system and/or components as shown in the figures, nor is every component of each embodiment shown where illustration is not required to allow one of ordinary skill to understand the system and/or components.

DETAILED DESCRIPTION

Various terms relating to aspects of the present disclosure are used throughout the specification and claims. Such terms are to be given their ordinary meanings in the art, unless otherwise indicated. In order for the present disclosure to be more readily understood, certain terms are first defined below. Additional definitions for the following terms and other terms are set forth throughout the specification.

As used herein, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, unless otherwise clear from context, the term "a" may be understood to mean "at least one." As used in this application, the term "or" may be understood to mean "and/or." In this application, the terms "comprising" and "including" may be understood to encompass itemized components or steps whether presented by themselves or together with one or more additional components or steps.

As used herein, the term "bubble" is used to describe the gas component of the activated liquid-gas mixture. The bubbles can be visible or so small as to be invisible, e.g., dissolved gas molecules. The bubbles can take to form of a foam or be part of turbulent liquid-gas flow. However, within the bubbles at least a portion of the gas molecules have been excited to a "plasma" state in which individual atoms or molecules have been stripped of at least some of their orbital electrons.

"Connected," and "coupled," as used herein, refers to directly coupling (i.e., connecting) one element (i.e., output) of a system or component to another element (i.e. input) by any suitable means available, such as, for example, through tubing. Optionally, other intervening elements may also be present.

"Color," as used herein, is broadly defined as a detectable property determined by a substance's electromagnetic absorption and/or emission in the visible spectrum.

"Colorless," as used herein, refers to when essentially no color can be detected apart from the normal coloration of the surroundings (such as skin or other tissue) by the naked eye under normal lighting conditions, for example, diffuse sunlight or standard artificial lighting.

"Dielectric barrier" discharge as used herein refers to an electrical discharge between electrodes separated by a dielectric material. For example, one or both electrodes can be coated with a dielectric material.

"Dislodged," as used herein, refers to the release of tattoo ink particles from local skin cells and tissue structures such as cells, membranes, and/or tissues, typically found in the dermis. As used herein, "Dislodge," "Dislodged," "Dislodgement," or other variations also encompass degradation of tattoo ink particles.

"Degrade," "Degraded," "Dislodgement," and the like as used herein, refers to the dislodgement of tattoo particles by the breakdown of the organic and/or inorganic components of tattoo ink particles due to interaction with the applied cold plasma energy via processes that include, but are not limited to, oxidation, reduction, fragmentation, electron decomposition, ion decomposition, or other degradation pathways. Degradation generally refers to a breakdown of a colored organic pigment, dye, or chromophore and/or to the breakdown of the particle size of colored inorganic ink particles which causes them to become colorless. Degradation can come about through the disruption of crystals or amorphous masses of elements such carbon, or by the breaking of chemical bonds in organic or inorganic compounds.

"Pigment, dye, or chromophore," as used herein, are terms that refer to organic and/or inorganic substance(s) which are colored and impart color to a tattoo ink. The color may result from substances which contain heavy metals such as mercury (red), lead (yellow, green, white), cadmium (red, orange, yellow), Chromium (green), cobalt (blue), aluminum (green, violet), titanium (white), copper (blue, green), iron (brown, red, black), barium (white), substances which contain metal oxides such as ferrocyanide and ferricyanide (yellow, red, green, blue), substances such as organic chemicals/compounds such as azo-containing chemicals (orange, brown, yellow, green, violet), naptha-derived chemicals (red), substances such as carbon (i.e., soot or ash) for black ink, and other color compounds which may contain antimony, arsenic, beryllium, calcium, lithium, selenium and sulfur. The pigments, dyes, or chromophores of a tattoo ink are typically dispersed or suspended in a carrier medium which together are delivered to the dermis. The most typical carrier constituents are ethyl alcohol and water, but may be denatured alcohols, methanol, rubbing alcohol, propylene glycol, and/or glycerin.

"Plasma," as used herein, connotes a state of matter in which one or more atoms or molecules have been subjected to sufficient energy to strip at least some of their orbital electrons. The transition from gas to plasma is also referred to as ionization.

"Invisible," as used herein, refers to the state of tattoo inks that show essentially no color which can be detected (such as in a tissue) apart from the normal coloration of the surroundings (such as skin or other tissue) by the naked eye under normal lighting conditions, for example, diffuse sunlight or standard artificial lighting.

"Non-discernible and undetectable," are used interchangeably and refer to a substance (i.e., tattoo ink) rendered invisible to the naked eye under normal lighting conditions, and also invisible to the naked eye, or a device, under any other lighting conditions.

"Removal" of a tattoo as used herein refers to any reduction of the visible appearance of a tattoo. Removal can mean rendering a tattoo non-discernible and undetectable or simply rendering a tattoo less noticeable in its appearance.

"Substantially" refers to a qualitative condition of exhibiting total or near-total extent or degree of a characteristic or property of interest. One of ordinary skill in the art will understand that electrical properties rarely, if ever, go to completion and/or proceed to completeness or achieve or avoid an absolute result. Substantially is therefore used herein to capture a potential lack of completeness inherent therein. Values may differ in a range of values within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than). For example, values may differ by 5%.

"Tattoo," as used herein, refers to a portion of skin, typically the dermis, which has tattoo ink particles embedded or trapped within.

"Uniform" refers to a qualitative condition of exhibiting similarity in a characteristic or property of interest. "Uniform" is therefore used herein to capture a degree of substantial similarity. Values may differ in a range of values within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than). For example, values may differ by 5%.

The methods for tattoo removal described herein are based on application of a DC pulsed or high frequency AC at a sufficient strength and duration to form plasma gas bubbles capable of dislodging or degrading tattoo ink particles trapped within a subject's dermis and extraction of the mobilized particles and/or degradation products from the subject's dermis. The method includes the steps of: (i) dislodging and/or degrading tattoo ink particles by applying electrical energy to a subject's tattooed dermis; (ii) mobilizing the dislodged and/or degraded ink particles and by-products thereof; and (iii) extracting the dislodged and/or degraded ink particles and by-products thereof from the subject's dermis to render the tattoo undetectable, invisible, and/or non-discernible.

FIG. 1 illustrates a process according to the invention in which a needle 20 is used to pierce the epidermis 11 and deliver plasma gas bubbles 32 to a target tattoo region with the dermis 12. In this region, tattoo ink particles 14 are present (typically entrapped in cellular structures 16). The needle delivers an activated liquid-gas mixture to the target region such that plasma gas bubbles can act upon the cellular structures that are holding the ink particles and dislodge and/or degrade them.

As further illustrated in FIGS. 1A-1D, the activated liquid gas mixture is delivered to the tattooed dermis 12 of a subject and induces dislodgement of ink particles 14 trapped by the cells, membranes, and/or other tissue structures 16 of the dermis 12 which are holding the ink particles 14 in place. The plasma (e.g., plasma gas bubbles can be delivered by any suitable means known. In preferred embodiments the plasma 10 is delivered to the dermis 12 via one or more needle or probe-like structures 20 that can penetrate the subject's tattooed skin. Those skilled in the art will be able to determine the penetration depth of the one of more needle or probe-like structures to deliver the plasma to the tattooed dermis.

It is believed that the plasma gas bubbles delivered to a subject's tattooed dermis interact with constituents present within the dermis such as, but not limited to, macrophages, fibroblasts, other cells, collagen fibers, and capillaries which have trapped the tattoo ink particle, in a sufficient amount to effectively disrupt the local dermal skin cells and tissue structures holding the particles and dislodge the trapped tattoo ink particles from the dermis and surrounding tissues. The plasma also may induce degradation of the ink particles, which are composed of organic and/or inorganic pigments, dyes, and/or chromophores and give color to the ink particles. Such degradation can result from the interaction of the plasma with the organic and/or inorganic components of the ink particles to degrade them via such processes as oxidation, reduction, fragmentation, electron decomposition, ion decomposition, or other degradation pathways.

In preferred embodiments, the plasma both dislodges the trapped ink particles without causing a significant amount of thermal or other type of irreparable damage to the subject's dermis or surrounding tissue.

In some embodiments of the method, the exposure time of the dermis to the plasma gas bubbles needed to dislodge and degrade the tattoo ink particles can be as short as one microsecond, but is more preferably a longer period of time, in the range from about one microsecond up to about one hour. In some embodiments, the plasma effectively degrades and dislodges the ink particles at the point of exposure within a period of time of 60 minutes or less, more preferably 10 minutes or less. In certain embodiments, the plasma may effectively dislodge and degrade all or a portion of the tattoo ink particles within a single tattoo removal treatment. In other embodiments, multiple treatments using plasma according to the methods described may be applied. The number of treatments depends on factors such as the area/size and complexity of the tattoo (for example, multi-colored and/or multi-layered tattoo and the age and settling of tattoo inks into lower portion of dermis over time) and on the health of the individual and/or individual's skin. In some non-limiting embodiments, tattooed skin having an area of up to 5 square inches may be treated in as little as one treatment. For tattoos having a larger surface area/size and/or complexity, repeated treatments may be applied with an intervening period time passing between treatments, such as up to one week, up to two weeks, up to three weeks, up to one month, up to two months, or up to three months; longer periods of time may pass between treatments as needed. In preferred embodiments of the method, the temperature of the dermis or other surrounding tissues is not increased by exposure to the plasma.

In certain other embodiments, the temperature of the dermis or other surrounding tissues when exposed to a treatment is not increased at all or significantly, only increasing by about 1 to about 5° C. above normal body temperature, which is below the temperatures needed to induce any significant amount of thermal damage or pain. The application of plasma to the dermis for tattoo removal is not expected to produce blanching and/or bleaching of the subject's natural skin color or pigmentation.

Referring again to FIG. 1 and FIGS. 1A-1D, the dislodged ink particles 14, and/or degradation by-products thereof, are mobilized in a mobilization step to remove them from the subject's dermis and surrounding tissues 12 prior to their recapture by the natural protection mechanisms of the skin, which can result in a re-tattooing effect. In some embodiments, the mobilization step involves the delivery of a pharmaceutically acceptable mobilization fluid 24, preferably through the same one or more needle or probe-like structures used to deliver the plasma 22. The mobilization fluid 24 facilitates the removal of the dislodged and degraded ink particles 14 and by-products thereof from the dermis 12. The mobilization fluid delivered to the plasma treated dermis is extracted in a subsequent extraction step which can be accomplished by any suitable means, such as by the application of suction. Suction, as used herein, refers to at least a partial vacuum created at the ends of the one or more needle or probe-like structures described above, such that the mobilization fluid containing the dislodged and degraded ink particles 26 is drawn away and extracted from the dermis and surrounding tissues. In some embodiments, suction is applied as a continuous suction or, alternatively, suction can be applied as a non-continuous pulsing suction. In some embodiments, no mobilization fluid is administered during or after the treatment and the dislodged ink particles and degradation by-products thereof are removed by extraction (i.e., suction) of natural bodily fluid(s) containing the particles and by-products from the dermis and/or surrounding tissue during the extraction step.

In preferred embodiments, all or a portion of the dislodged and/or degraded tattoo ink particles are extracted from a tattoo during the extraction step. By removing dislodged and degraded tattoo ink particles, the tattoo on skin treated according to the method described becomes undetectable, invisible, and/or non-discernible. By definition, an effective amount of plasma is applied to cause the colors in the original tattoo in the treated area to become undetectable, invisible and/or non-discernible. In some embodiments, treatment of the tattoo ink particles with plasma may render the ink particles down to their colorless atomic, molecular, and/or gaseous components, such as carbon dioxide or water, and the colorless components may not require removal or extraction from the skin if the tattoo has otherwise been rendered undetectable, invisible, and/or non-discernible to the naked eye. In such embodiments, the portion of dislodged and degraded ink particles and degradation by-products thereof which are rendered into colorless components and which remain in the dermis may be absorbed through the interstitial fluid of the body. In such embodiments the method involves dislodging and degrading tattoo ink particles by applying plasma to a subject's tattooed dermis; wherein the energy is applied in an effective amount to a subject's dermis to render the tattoo undetectable, invisible, and/or non-discernible.

The application of the steps of mobilizing the dislodged and/or degraded ink particles and by-products thereof and extracting the dislodged and/or degraded ink particles and by-products thereof from the subject's dermis as described above are optional and determined at the discretion of the skilled technician or operator applying the tattoo removal method to the subject's tattooed skin. Depending on the extent to which the tattoo has been rendered undetectable, invisible, and/or non-discernible by plasma treatment alone the operator/technician may apply steps (ii) and (iii) as shown in FIG. 1 in order to further render the tattoo undetectable, invisible, and/or non-discernible.

In some embodiments, the extraction of the degraded and/or dislodged ink particles and by-products thereof from the subject's skin is highly desirable as these may have toxic properties. In contrast to laser-based tattoo removal techniques wherein inks and degradation by-products thereof may remain in situ and/or become absorbed by the subject's body, the methods described herein can result in extraction of these foreign inks and components in order to prevent their absorption by the subject and any potentially harmful effects on health.

In some embodiments of the method the steps of dislodgement, mobilization, and extraction, as shown in FIG. 1, are performed in sequence as shown, for example, (i)→(ii)→(iii). In embodiments wherein the steps are applied sequentially, the steps are performed so as to provide at least one complete cycle which includes the dislodgement, mobilization, and extraction steps (i), (ii), and (iii). The complete cycle may be repeated any number of times as necessary to effectively remove the tattoo by dislodging and degrading tattoo ink particles from the subject's dermis and tissue. The preferred number of cycles which may be applied are typically in the range of one to 100 cycles, or more.

In certain other embodiments, all of the steps are applied concurrently. In a non-limiting example, the dislodgement (application of plasma to tattooed dermis), mobilization, which may include the introduction of a mobilization fluid to the dermis, and the extraction step, which involves removal of the mobilization fluid containing the dislodged and degraded ink particles and degradation by-products thereof, or in some instances where no mobilization fluid is used, removes the dislodged and degraded ink particles and degradation by-products thereof directly.

In some other embodiments, the steps of dislodgement and mobilization occur concurrently and are followed by the extraction step and form a cycle which is performed at least one or more times, as necessary to remove the tattoo ink from the subject's dermis and rendering the tattoo undetectable, invisible, and/or non-discernible.

In certain embodiments, the method described above can further include a pretreatment of the surface of the tattooed skin with a mobilization fluid, e.g., water saline or the like. In certain embodiments, an antibiotic solution can be pre-applied in order to prevent the introduction of infectious organisms present on the surface to the skin into the dermis during treatment. In other embodiments, the pretreatment may also include application of topical anesthetics to the surface of the skin in order to prevent or alleviate any potential discomfort during the treatment.

In some embodiments, electrical energy can be applied in conjunction with "cold plasma" that, as used herein refers to a non-thermal or atmospheric plasma, generated by subjecting a gas(es) to a strong electrical field with a rapidly changing polarity to create a plasma which may contain electrons, highly energetic positively or negatively charged ions, and chemically active species such as ozone, hydroxyl radicals, nitrous oxides and other excited atoms or molecules. In particular, cold or non-thermal plasmas are created at or near standard atmospheric pressure and have temperatures which are close to or near room temperature which are non-damaging when applied to tissue. Contacting tissue with a cold plasma does not increase the tissue temperature at all or significantly, typically only by a few degrees or less.

Methods for generating cold plasma as described herein are well-understood by those skilled in the art. Exemplary methods to produce atmospheric cold plasmas include, but are not limited to, arc discharge, corona discharge, dielectric barrier discharge (DBD), capacitive discharge, and piezo-electric direct discharge. Typically, such plasmas are generated from a gas or a mixture of gases which include, but are not limited to, air, oxygen, nitrogen, helium, argon, neon, xenon, and krypton. In certain embodiments, the cold plasma is generated from a mixture of argon and oxygen or a mixture of helium and oxygen. Conditions such as the power, flow rate of gas(es), and the ratio of gases in mixtures used to generate a cold plasma can be optimized as needed to achieve the desired properties of the cold plasma, such as to ensure it is at or near room temperature.

In certain embodiments the power used to generate the plasma is in the range of about 80 W to about 150 W. In some preferred embodiments, the gas flow rates are in the range of about 0.00001 to about 15 L min$^{-1}$. The relative percentages of the one or more gases present in the mixture can be any suitable relative percentage necessary to achieve a cold plasma. In preferred embodiments, wherein the plasma generating mixture of gases is composed of oxygen mixed with argon or helium, the percentage of oxygen in the mixture is preferably in the range of about 0.1% to about 5%.

The cold plasma stream generated according to the methods described herein may be delivered and output into the dermis via one or more needle or probe-like structures as a continuous cold plasma jet stream or can be delivered as a discontinuous pulsed cold plasma jet stream. It should be apparent that the details described herein are non-limiting and that other suitable conditions and parameters can be selected and utilized in order to generate and deliver the cold plasma to the dermis.

In certain embodiments, non-limiting examples of the mobilization fluid include sterile water, saline solution, or buffered aqueous solutions. One skilled in the art can readily determine a suitable saline and buffer content and pH for a mobilization fluid/solution to be administered to the dermis of a subject. Representative examples include phosphate buffered saline ("PBS"), Ringer's solution, and sterile physiological saline (0.15 M NaCl).

In certain embodiments, the mobilization fluid can further include surfactants which improve the mobility and removal efficiency of the degraded ink particles and/or degradation by-products thereof. Preferred surfactants include those approved by the U.S. Food and Drug Administration ("FDA") as GRAS ("generally regarded as safe") excipients for injection. In certain other embodiments, the mobilization fluid can also include suitable local anesthetics, anti-infective agents, antiseptic agents, anti-inflammatory agents, and combinations thereof.

Surfactants which can be included in the mobilization fluid may be anionic, cationic, amphoteric, and non-ionic surfactants which are pharmaceutically acceptable for use in a human subject. Anionic surfactants include di-(2 ethylhexyl)sodium sulfosuccinate; non-ionic surfactants include the fatty acids such as butyric acid, valeric acid, caproic acid, enanthic acid, caprylic acid, pelargonic acid, caprylic acid, undecylic acid, lauric acid, tridecylic acid, myristic acid, pentadecylic acid, palmitic acid, heptadecylic acid, stearic acid, nonadecanoic acid, arachic acid, isocrotonic acid, undecylenic acid, oleic acid, elaidic acid, sorbic acid, linoleic acid, linolenic acid, arachidonic acid and esters thereof; surfactants in the amphoteric group include substances classified as simple, conjugated and derived proteins such as the albumins, gelatins, and glycoproteins, and substances contained within the phospholipid classification. Amine salts and quaternary ammonium salts within the cationic group also comprise useful surfactants. Synthetic polymers may also be used as surfactants and include compositions such as polyethylene glycol and polypropylene glycol. Hydrophobic surfactants can be used to improve the removal of hydrophobic ink particles and degradation by-products thereof. Hydrophilic surfactants can be used to improve the removal of hydrophilic ink particles and components and degradation by-products thereof. Amphiphilic surfactants can be used to improve the removal of amphiphilic ink particles and components and degradation by-products thereof.

In some embodiments, anesthetic agents can be included in the mobilization fluid such as local anesthetics, such as but not limited to, -caine anesthetics such as bupivacaine, ropivacaine, dibucaine, procaine, chloroprocaine, prilocaine, mepivacaine, etidocaine, tetracaine, lidocaine, and xylocaine, and mixtures thereof which can be used alone or in combination with other analgesics.

In some embodiments, antiseptic agents can be included in the mobilization fluid. Exemplary antiseptic agents can be composed of any anti-infective compound that prevents the growth of and/or kills infectious organisms. Antiseptic agents are preferably non-irritating and hypoallergenic, such that they do not cause any adverse reactions to the dermis and surrounding tissue of the subject.

"Anti-infective agent," as used herein, refers to common antibacterial, antifungal, and antiviral agents which can be include a chemical substance or group of chemical substances that inhibit the growth of, or destroy microorganisms, fungi, and viruses and are used chiefly in the treatment of infectious diseases. In some preferred embodiments, antibiotics can be included in the mobilization fluid. These may help to prevent infection in the dermis and surrounding tissues of the site of tattoo removal. Exemplary antibiotics include, but are not limited to, chloramphenicol, chlortetracycline, clindamycin, erythromycin, gramicidin, gentamicin, metronidazole, mupiroicin, neomycin, polymyxin B, bacitracin, doxycycline, ampicillin, penicillin, silver sulfadiazine, tetracycline, erythromycin, or combinations thereof.

In some embodiments, anti-inflammatory agents can be included in the mobilization fluid. Anti-inflammatory agents can provide beneficial effects during tissue healing and repair. Anti-inflammatory agents can include, but are not limited to, steroidal anti-inflammatory agents such as dexamethasone, budesonide, beclomethasone, and hydrocortisone and non-steroidal Anti-Inflammatory Agents (NSAIDS). NSAIDS typically inhibit the body's ability to synthesize prostaglandins. Prostaglandins are a family of hormone-like chemicals, some of which are made in response to cell injury. Specific NSAIDS approved for administration to humans include naproxen sodium, diclofenac, sulindac, oxaprozin, diflunisal, aspirin, piroxicam, indomethacin, etodolac, ibuprofen, fenoprofen, ketoprofen, mefenamic acid, nabumetone, tolmetin sodium, and ketorolac tromethamine. Anti-Inflammatory agents are a well-known class of pharmaceutical agents which reduce inflammation by acting on body mechanisms (Stedman's Medical Dictionary 26 ed., Williams and Wilkins, (1995); Physicians' Desk Reference 51 ed., Medical Economics, (1997)).

In some embodiments, the mobilization fluid may further contain additional agents, such as preservatives, viscosity adjusting additives, and other potentially beneficial materials, such hydrogen peroxide or hemoglobin derived oxygen carriers. Any volume of the formulated mobilization fluid may delivered as needed to the treated dermis in order to effectively facilitate removal of the dislodged and degraded ink particles and by-products thereof during the extraction step. In preferred embodiments the total volume of mobilization fluid used to remove dislodged and degraded ink particles and degradation by-products thereof is less than about 10 mL, more preferably less that about 5 mL, even more preferably less than about 2 mL, and most preferably less than about 1 mL.

Plasma Generating Component

In one non-limiting embodiment as shown in FIG. 2, a system 50 is shown including liquid source 52, a gas source 54 and a mixer 56. The system can optionally include a pump 58 and/or a temperature regulator 60. The system can be operated under the control of a controller 62. The system can operation, in one example, to deliver a liquid-gas mixture to a first end of plasma generator including a tubular element 51. To generate a plasma within the gas component, a power source 64 (also under control of the controller 62) delivered a DC and/or AC current to one or more electrodes 65. In certain embodiments, the electrode can be a dielectric barrier discharge electrode. In other embodiments, the discharge can be induced by a piezoelectric transducer.

The system can further include an optional vacuum source 68 to extract dislodged and/or degraded tattoo ink particles. (The vacuum or suction source can also be a stand alone instrument in some embodiments of the system).

The system can further include an alternative liquid supply 66. This alternative liquid supply can provide an additional source of mobilization fluid that can be provided to the target tattoo region before, during or after plasma treatment. In another embodiment, plasma generator can act first on gas from gas source 54 to generate a gas plasma which is then mixed with a liquid component at or near the exit end of the plasma generator to create the activated liquid-gas mixture.

The activated liquid-gas mixture can then be delivered to treatment head 20. e.g., one or more hollow needles configured to penetrate the epidermis 11 and deliver the plasma to the dermis where it can act upon tattoo ink particles 14 and/or cellular structures 16m in which the ink particles are embedded, encased or otherwise bound.

In the present invention, cold plasma is generated in mixture of at least one liquid and at least one gaseous substance. The cold plasma can be formed by corona discharge or dielectric barrier discharge.

An apparatus for generating cold plasma via excited gas bubbles can comprise a plasma discharge unit with a first end and a second end. A source of liquid and a source of gas can be fed into a mixing unit arranged upstream of the first end of the plasma discharge unit to deliver the liquid with entrained gas to the discharge unit. The second end of the discharge unit can be coupled to a hollow needle or array of needles to deliver the liquid with cold plasma gas bubbles to a target site. In certain embodiments, the plasma discharge unit is tubular. The discharge unit and the needle or needle array can be integrally formed together.

In the exemplary embodiment of FIG. 2, one or more electrodes are coupled to an outer wall of a discharge unit for generating a high energy alternating electric field within the discharge unit. The controller 52 is connected at least to the mixing unit 56 and the electrodes 65. The controller 52 can determine the proportions of the at least one gaseous substance and of the at least one liquid substance or of the various liquid substances in the mixing unit, so that a desired mixture enters the plasma discharge unit. The controller can also adjust the voltage applied to the electrodes. From the mixing unit, the mixture of at least one gaseous substance and at least one liquid substance can be pumped into the discharge unit at the first end. The transfer into the tubular discharge unit by means of the pump can also be controlled by the controller.

The applied alternating electric field is preferably strong enough that a cold gas discharge can be ignited inside the gas bubbles in the liquid in the plasma discharge unit. The intensity of the interaction can be controlled by the amplitude and frequency of the applied alternating electric field, the mixing ratio and the total surface area of the interfaces between the gaseous and liquid phases. Many liquids have a dielectric constant significantly greater than 2. Typical gases have a dielectric constant of nearly 1. Water, for example, has a dielectric constant of 80. This difference in dielectric constant between a gaseous substance and a liquid substance can cause a sharp drop in the applied electrical potential in the gas bubble. As a result, the electric field strength in the gas bubbles is particularly high.

In certain embodiments, the mechanism for generating the alternating electric field within the tubular discharge unit can be a piezoelectric transducer or transformer. In other embodiments the mechanism can be a dielectric barrier electrode. In either embodiment, at least one electrode is coupled to the plasma discharge unit. The electrode can be connected to a voltage source and the voltage applied is controlled by the controller 52. An electric field can be formed within the discharge unit by the at least one electrode 65.

The electric field can extend beyond the second end of the tubular discharge unit. This allows the discharge area to extend beyond the second end of the discharge unit or beyond a needle or other treatment applicator 20 provided at the second end of the discharge unit.

The treatment applicator can be configured in such a way that a spray at the second end of the tubular discharge unit, or at the end of a needle or nozzle, is dispersed or atomized by electrostatic charging. In certain embodiments, the spray is delivered to a tattooed region of the dermis.

The mixing unit may be connected to at least one source or reservoir for the at least one gaseous substance and to at least one source or reservoir for the at least one liquid substance. A plural reservoirs for the liquid and/or gaseous substance can be connected to the mixing unit.

A temperature control device (a heater or cooling unit) 60 can also be to the tubular discharge unit by means of which the active species in the tubular discharge unit can be heated and/or cooled. With the temperature control device 60, the temperature of the mixture of the at least one gaseous substance and the at least one liquid substance in the tubular discharge unit can thus be brought to a predetermined value. In tattoo removal applications, the discharge can be controlled such that the plasma is maintained at or near room temperature (e.g., a cold plasma). The discharge unit can be fluidly connected to a target tattoo region via the second end directly or via a delivery device, such as one or more hollow needles, a nozzle or a cannula.

The inventive method for degrading tattoo ink particles can be characterised in that at least one gaseous substance is mixed with at least one liquid substance in a mixing unit. The mixture passes from the mixing unit into a first end of a plasma discharge unit. The mixture can be pumped from the mixing unit into the first end of the discharge unit. In the discharge unit, bubbles of the gaseous substance are exposed to an intense electric field. In certain embodiments, a controller generates an alternating electric field which is applied to the mixture of the at least one gaseous substance and of the at least one liquid substance. The gas discharge is ignited in the bubbles formed by the gaseous substance. The mixing ratio of the at least one gaseous substance and the at least one liquid substance can be adjusted or set by the controller. The controller 52 can also set the applied strength of the alternating electric field. The mixing ratio and the total surface area of the interfaces between the gaseous and liquid phases can be adjusted by means of the intensity of the interaction, the amplitude and the frequency of the applied alternating electric field. The active species generated by the alternating electric field are fed to a target tattoo region via a second end of the discharge unit.

The intensity of electric field generated within the plasma discharge unit can be controlled by adjusting a DC voltage source. The gaseous and/or liquid substance can be forced through the needle or needle array in such a way that a stream or dispersed spray is delivered to a target dermal region where tattoo ink particles are located. The flow of liquid with entrained plasma gas bubbles from the needles or tubular discharge unit can be continuous or discontinuous.

The inventive methods can be employed to stimulate the skin and/or subcutaneous areas with an alternating electric field and the cold plasma. It is also possible to flush a subcutaneous cavity with an activated liquid or mixture of different liquids (liquid substances) or an activated gas mixture or a mixture of at least one gaseous substance and at least one liquid substance. Furthermore, an electrophoretic effect may occur which promotes the mobility of particles in the dermis. The method according to the invention can also be used to degrade, dislodge, rinse, wash out or otherwise render tattoo ink particles in a target dermal region less discernible.

The method according to the invention allows the chemical properties of tattoo ink particles to be changed when they comes into contact with the gas bubbles of cold plasma. For example, biological structures in the skin or elsewhere, such as various cells, collagens, or other structural proteins, can be influenced and treated. Non-biological material in the skin, such as tattoos or other foreign bodies, can be degraded or removed.

The gaseous substance used in the method according to the invention may be, for example, ambient air, a noble gas, oxygen, nitrogen, carbon dioxide or a mixture of these gases. The liquid substance may be e.g. water, a salt solution, an alcohol, $H_2O_2$ or a mixture of the above liquids. Additives such as antibiotics, reactive monomers, surfactants or foaming agents can also be added to the liquid substance.

In certain embodiments, discrete bubbles of the gaseous substance form in the liquid substance within the plasma discharge unit. Here the ratio between the proportion of the gaseous substance and the proportion of the liquid substance is controlled in such a way that individual discrete bubbles form within the liquid and are activated as a plasma or highly active gas species. The temperature of this mixture of the liquid substance and the activated gaseous substance can be adjusted to a desired value by heating or cooling.

At least one component, the liquid or the gaseous component, can be collected after passing through the discharge zone and can be passed on to further use. The apparatus according to the invention can be adapted or controlled to change the density and volume of the gaseous and/or liquid substances in the tubular discharge unit. The tubular discharge unit can also be in the form of a capillary.

By means of the present invention, a discharge system can be used for heterogeneous mixtures of at least one gas and at least one liquid, or also of special liquids without the admixture of a gas, to produce active species in the gas or liquid phase. The active species can be used in various applications such as liquid sterilization, surface treatment, coating, human or animal skin treatment such as direct subepidermal CAP treatment, and many others.

Figure 3:
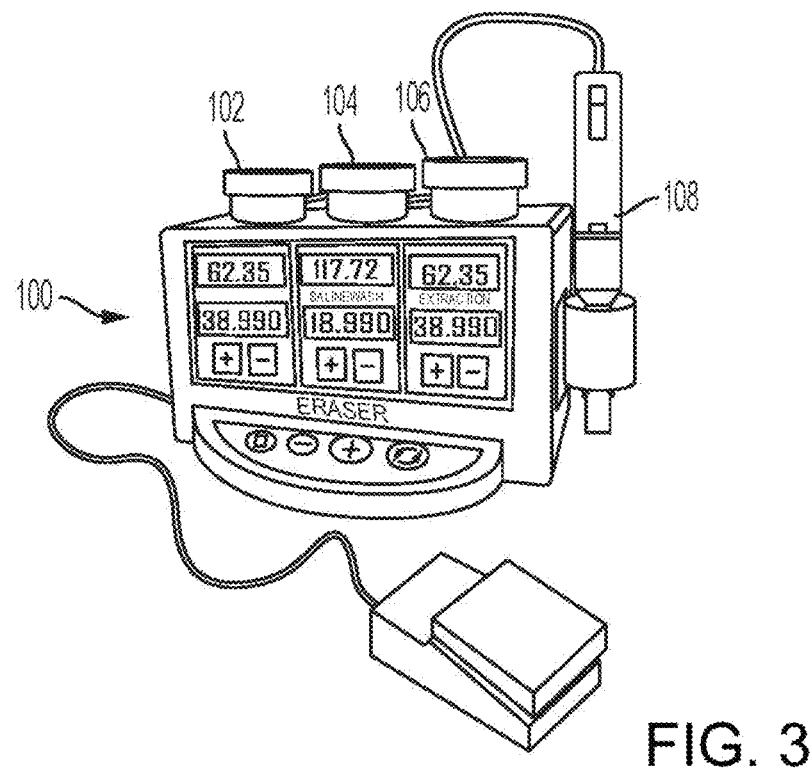
FIG. 3 shows another non-limiting example of a tattoo removal system capable of applying an activated liquid-gas mixture to a target tattoo region.

In another non-limiting embodiment, as shown in FIG. 3, the system for tattoo removal includes a main housing 100 wherein: an plasma generation component 102; a fluid delivery component 104; and a fluid extraction component 106 are integrated. In some other embodiments, the fluid delivery component may be excluded from the system. The system is connected and coupled to a free-standing treatment component 108, which may be in the form of pen or wand-like component. The housing of the tattoo removal system also includes additional components, as needed, to power the aforementioned 102, 104, and 106 components and the treatment component 108, so as to provide power from an electrical outlet or from one or more battery source(s). The main housing may further include one or more control unit(s), which may include input controls (i.e., knobs, buttons, foot pedals) and analog or digital displays which show parameters of the 102, 104, and 106 components in order to control and regulate each component's parameters prior to and during operation. In some embodiments, one (main) control unit may be used to control all the components, while in some other embodiments each component has its own individual control unit on the system's main housing.

In some other embodiments, the plasma generation component 102; a fluid delivery component 104; and a fluid extraction component 106 may be incorporated into a single combined treatment component 106. In some embodiments, the fluid delivery component may be excluded from the combined treatment component. A foot pedal 110 can provide means for controlling the plasma application, saline wash, and extraction.

Figure 3A:
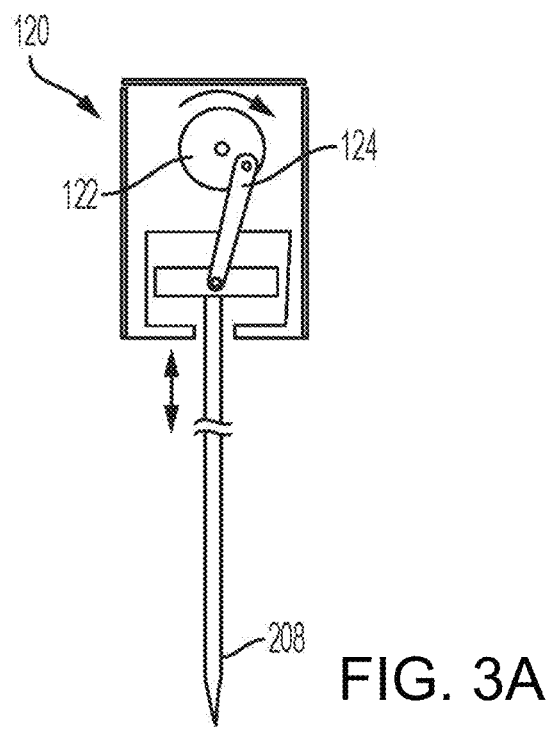
FIG. 3A is a schematic illustration of a kinetic applicator for use with systems according to the invention.

FIG. 3A is a schematic illustration of a kinetic applicator 120 that can be incorporated into the treatment components (handpieces) of the invention, including a motor 122 and cam mechanism 124 to imparting a vibratory or oscillating motion to the needle or active electrode 208.

The electrical power source component 64 may be a commercially available component which is adapted to be a part of the tattoo removal system described herein. The plasma generation component housed in the main system includes all necessary components required to provide a high frequency alternating current, or high repetition rate pulsed direct current to one or more skin-penetrating electrodes. Optional components relating to cold plasma formation can also include, but are not limited to, gas inputs, valves, regulators, pumps, gas mixing chamber/units, power systems. The conditions, such as the power, flow rate of gas(es), and the ratio of gases in mixtures used to generate a cold plasma can be controlled as needed to achieve the desired properties of the cold plasma, using the input control(s) connected and coupled to the plasma generation unit.

Typically, plasmas are generated from a gas or a mixture of gases which may include, but are not limited to, air, carbon dioxide, oxygen, nitrogen, helium, argon, neon, xenon, and krypton. In preferred embodiments, the cold plasma generation unit receives gas(es) from one or more gas sources. In some embodiments, the one or more gas sources may be in the form of free-standing replaceable gas tanks/cylinders or the one or more gas(es) may be from a source such as a gas outlet present on a wall and connected to a central gas source. In certain embodiments, the one or more gas sources are external to the main housing of the tattoo removal system and are coupled and connected to the one or more gas inputs of the plasma generation component of the system by any suitable means (i.e., gas regulator and gas tubing). In certain other embodiments, the one or more gas sources may be included within the housing of the tattoo removal system, if desirable. In preferred embodiments the power used to generate the cold plasma is in the range of about 80 W to about 150 W. In some preferred embodiments, the gas flow rates are in the range of about 0.00001 to about 15 L min$^{-1}$. The relative percentages of the one or more gases present in the mixture can be controlled by a gas mixing unit to achieve any suitable relative gas mix percentage necessary to achieve a cold plasma. In certain embodiments, wherein the plasma generating mixture of gases is composed of oxygen mixed with argon or helium, the percentage of oxygen in the mixture is preferably in the range of about 0.1% to about 5%.

The plasma generation component is coupled and connected using any suitable means and outputs/delivers the cold plasma generated to the treatment component for delivery to the tattooed dermis. The cold plasma stream generated may be controlled via the one or more input control units of the system. The plasma output by the component to the treatment component may be a continuous cold plasma jet stream or a discontinuous pulsed cold plasma jet stream. It should be apparent that the details described herein are non-limiting and that other suitable conditions and parameters can be selected and utilized in order to generate and deliver the cold plasma to the tattooed dermis. The delivery of cold plasma to the dermis via a treatment component, which may be in the form of a pen/wand, can be controlled by a skilled/trained operator or technician using an input control unit, such as a foot pedal.

In some embodiments, the plasma generation component as discussed above may be incorporated directly into the treatment component. In certain embodiments, the plasma generated in the treatment component is an air plasma and requires no external gas source. In certain other embodiments, one or more gas sources that are external to the treatment component are coupled and connected to one or more gas inputs of the treatment component by any suitable means (i.e., gas regulator and gas tubing). In certain other embodiments, the one or more gas sources may be included within the treatment component, if desirable.

Fluid Delivery Component

The fluid delivery component of the system includes one or more fluid reservoir units which can hold one or more liquids to be mixed with the ionized gas or to serve a separate mobilization fluid. The one or more reservoir units are coupled and connected to the treatment component of the tattoo removal system by any suitable means (i.e., tubing) in order to output the mobilization fluid to the treatment component. The mobilization fluid delivery component includes one or more controllable fluid pumps which deliver the mobilization fluid to the treatment component at a controllable flow rate. The flow rate of the fluid can be regulated by the one or more input controls or units coupled and connected to the fluid delivery component. In some embodiments the mobilization fluid is not pre-formulated but can be generated on-demand by mixing units which may form part of the fluid delivery component. Such mixing units are fed by the one or more fluid reservoir units which may contain the component fluids and other agents which form the desired mobilization fluid such as, but not limited to, sterile water, saline solution, buffered aqueous solutions and suitable local anesthetics, anti-infective agents, antiseptic agents, anti-inflammatory agents, and combinations thereof. The delivery of mobilization fluid to the dermis via the treatment component can be controlled by a skilled/trained operator or technician using an input control unit, such as a foot pedal.

In some other embodiments, the fluid delivery component, as described above, may be directly incorporated into a free-standing pen or wand-like component. In such embodiments, one or more disposable fluid cartridges which hold a given volume of pre-formulated mobilization fluid (described above) may be coupled and connected to the fluid delivery component to output the mobilization fluid to one or more needle or probe-like structures of the treatment component as described below. In such embodiments, the delivery of mobilization fluid to the dermis via the one or more needle or probe-like structures of the treatment component can be controlled by a skilled/trained operator or technician using an input control unit present on the treatment component.

Fluid Extraction Component

The fluid extraction component of the system includes one or more vacuum pumps and/or other components necessary for creating a vacuum or partial vacuum and is connected and coupled by any suitable means to the treatment component so as to create suction used to extract the mobilization fluid delivered to the dermis during tattoo removal treatment and draw/extract the mobilization fluid containing dislodged and degraded ink particles and by-products thereof, and tissue by-products thereof away from the dermis and surrounding tissues of the subject. In some embodiments of the system which exclude a fluid delivery component and mobilization fluid, the fluid extraction component can remove the dislodged degraded tattoo ink particles which may be present in the natural fluids of the dermis or surrounding tissue directly. In some embodiments, suction created by the extraction component is applied as a continuous suction or, alternatively, the suction can be applied intermittently. The application of suction to the dermis and/or surrounding tissue can be controlled by a skilled/trained operator or technician using an input control unit, such as a foot pedal.

In some other embodiments, the fluid extraction component, as described above, may be directly incorporated into a free-standing pen or wand-like component. In such embodiments, the application of suction to the dermis and/or surrounding tissue can be controlled by a skilled/trained operator or technician using an input control unit present on the treatment component, which may be in the form of a pen or wand.

Treatment Component

Figure 4:
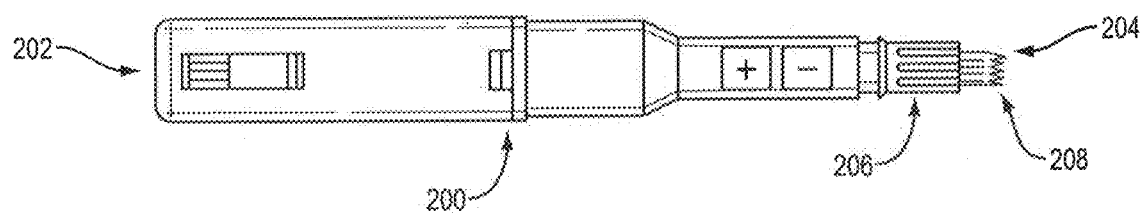
FIG. 4 shows a non-limiting example of a treatment component in the form of a pen or wand which includes a treatment end which contains one or more needle or probe-like structures as part of a disposable cartridge.

The treatment component can be coupled and connected to the components discussed above using any suitable means known. Alternatively, the treatment component can have incorporated into it at least one or more of components as described above. The treatment component can be in the form of a pen or wand 200 and is formed of a main body as shown in FIG. 4. The treatment component is also referred to herein as a pen/wand component. The treatment component includes suitable mechanical components, as needed, to deliver electrical energy (and, optionally, cold plasma) and mobilization fluid into the dermis and to apply suction to the dermis. One end 202 of the treatment component may include one or more inputs and outputs (not shown) which are connected/coupled to the other components of the system as described above when these components are external to the treatment component. For example, the inputs can receive the electrical energy and mobilization fluid and the output can receive the mobilization or other body fluid extracted from the dermis or surrounding tissue during tattoo removal. The opposite end of the treatment component includes a treatment end which can output and deliver the activated liquid-gas mixture and/or mobilization fluid into the dermis. The treatment end 204 can also receive extracted mobilization fluid, or other natural body fluids, which contain dislodged and degraded tattoo ink particles during treatment of the dermis and surrounding tissue.

Kinetic Movement

In certain embodiments, the treatment end 204 is formed of a cartridge unit 206 which contains one or more needle or probe-like structures 208 which penetrate the subject's tattooed skin. The treatment end of the treatment component includes one or more needle or probe-like objects 208 which can penetrate skin and preferably form a part of a removable, disposable, and/or replaceable unit cartridge. The one or more needle or probe-like structures 208 can be made of either plastic, metal or a combination thereof. In some non-limiting embodiments, the removable, disposable, and/or replaceable cartridge includes one, two, three, four, five, six, seven or more needles. The depth of penetration of the one or more needle or probe-like structures, present in the needle cartridge, into the skin is preferably to the depth of the dermis of the subject's tattooed skin but may be adjusted by a skilled/trained operator or technician as needed to apply the tattoo removal treatment method using the system described herein. The one or more needle or probe-like structures 208, which penetrate into the tattooed dermis, oscillate or pulse during tattoo removal treatment via a mechanical process, such as a piston like drive which pulses and/or oscillates the needles in and out of the dermis at varying speeds. In certain other embodiments, the one or more needle or probe-like structures 208, which penetrate into the tattooed dermis are fixed and do not pulse or oscillate.

In some embodiments, the one or more needle or probe-like structures oscillate or pulse and with each oscillation or pulse perform one or more functions of delivering electrical energy, delivering cold plasma, delivering mobilization fluid to the dermis, or extracting the mobilization fluid containing dislodged and degraded ink particles and by-products thereof, and tissue by-products thereof. In some embodiments each full or partial oscillation or pulse applies a particular function sequentially at a time and all the functions as described are performed so as to provide at least one complete cycle which includes the dislodgement, mobilization, and extraction steps. In certain other embodiments, all of the functions are applied concurrently during a given oscillation or pulse of the one or more needles. In some other embodiments, some, but not necessarily all of, the functions described form part of a cycle which is performed at least one or more times during a given oscillation or pulse of the one or more needles, as necessary to remove the tattoo ink from the subject's dermis and rendering the tattoo undetectable, invisible, and/or non-discernible.

As shown in FIG. 4, the one or more needle or probe-like structures 208 which are present at the treatment end 204 of a treatment component in the form of a pen/wand 200 can penetrate into the dermis and deliver electrical energy (and, optionally, cold plasma) and deliver and extract fluids to and from the dermis and surrounding tissue undergoing tattoo removal. In some embodiments, different needle/probe-like objects present on the treatment end can serve different functions, such as plasma delivery, fluid delivery, or fluid extraction. In some embodiments, a single needle/probe-like object may perform multiple or all of the aforementioned functions.

Figure 4A:
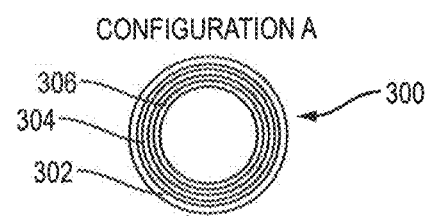
FIGS. 4A and 4B show front (4A) and side (4B) views of a multi-sheathed needle or probe-like structure formed of three concentric nested/embedded needle or probe-like structures forming inner, middle, and outer rings. The outer portion of the needle or probe-like structure includes optional openings.
Figure 4B:
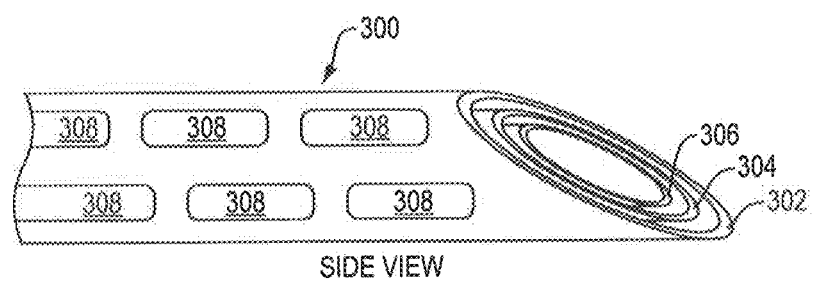

As shown in FIGS. 4A and 4B, each of the needle or probe-like structures of the removable, disposable, and/or replaceable unit cartridge can be formed of a multiple sheathed needle 300 which is formed from nested multiple concentric needles 302, 304, and 306.

In one non-limiting example as shown in the configuration of FIGS. 4A and 4B, a multi-sheathed needle or probe-like 300 is formed of three concentric nested/embedded needle or probe-like structures forming inner 306, middle 304, and outer rings 302. In some embodiments, the outer most ring 302 delivers cold plasma and optionally the outer most portion of the needle or probe-like structure includes suitable openings 308 on the outer side for delivering cold plasma to the dermis. In some embodiments, the middle ring 304 delivers mobilization fluid to the dermis. In some embodiments, the inner most ring 302 provides suction to the dermis to remove mobilization fluid containing dislodged and degraded tattoo ink particles and by-products thereof from the dermis. Any one or all of the concentric structures can serve as the active electrode for delivery of electrical energy.

Figure 5A:
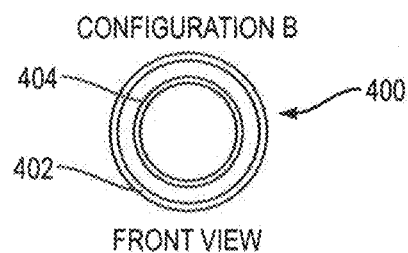
FIGS. 5A and 5B show front (5A) and side (5B) views of a multi-sheathed needle or probe-like structure formed of two concentric nested/embedded needle or probe-like structures forming inner and outer rings. The outer portion of the needle or probe-like structure includes optional openings.
Figure 5B:
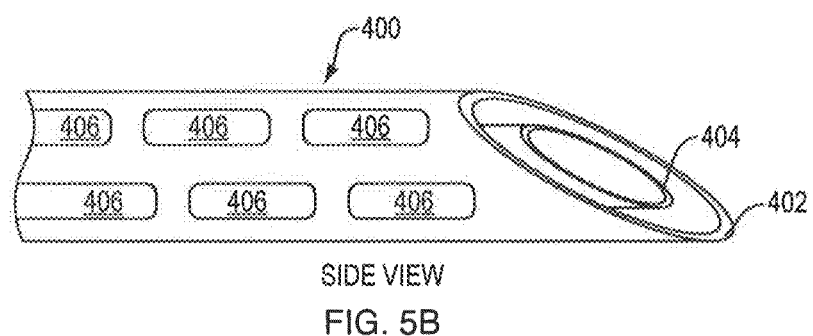

In another non-limiting example as shown in the configuration of FIGS. 5A and 5B, a multi-sheathed needle 400 is formed of two concentric nested/embedded needle or probe-like structures forming inner 404 and outer 402 rings. In some embodiments, the outer most ring delivers cold plasma and extraction fluid which are sequentially pulsed into the dermis. Optionally, the outer most portion 402 of the needle or probe-like structure can include suitable openings 406 on the outer side for delivering cold plasma to the dermis. In some embodiments, the inner ring 404 provides suction to the dermis to remove mobilization fluid containing dislodged and degraded tattoo ink particles and by-products thereof from the dermis. Again, anyone or both of the concentric structures can serve as the active electrode for delivery of electrical energy.

Figure 6A:
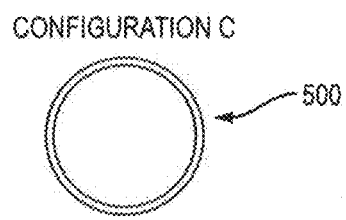
FIGS. 6A and 6B show front (6A) and side (6B) views of a single-sheathed needle. The outer portion of the needle or probe-like structure includes optional openings.
Figure 6B:
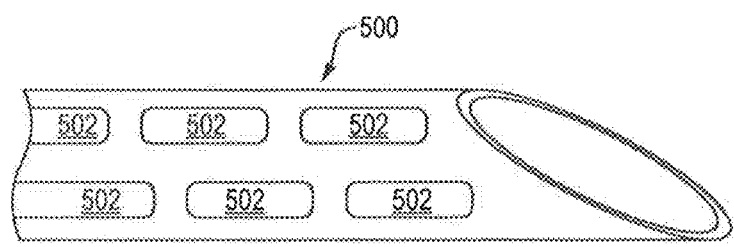

In another non-limiting example as shown in the configuration of FIGS. 6A and 6B, a single-sheathed needle 500 may be used in the cartridge. Optionally, the outer surface of the needle or probe-like structure 500 can include suitable openings 502 on the outer side for delivering cold plasma to the dermis. In a single sheath configuration, the cold plasma, mobilization fluid, and suction are sequentially applied to the dermis during treatment and the sheath itself is conductive for delivery of electrical energy to the target tattoo region.

As described above, the one or more needle or probe-like structures of the cartridge may each be formed of a multiple sheathed needle-like structure. One of ordinary skill will immediately recognize that the above examples are non-limiting and variations are permitted regarding the use of any of the sheaths present in the embedded/nested structure to achieve any of the plasma, fluid, or extraction functions as described above. In some embodiments, the rate of flow of cold plasma, mobilization fluid and rate of suction can be controlled by a computerized flow meter included in the treatment component.

In some embodiments, an input control, such as a foot pedal or button(s) present on the treatment component, may be used to activate, deactivate, and control all of electrical energy, cold plasma, dislodgement, mobilization and extraction components coupled and connected to the treatment component, or integrated within the treatment component which may be in the form of a pen/wand, at one time or may control the electrical energy, cold plasma, dislodgement, mobilization and extraction components individually. In some other embodiments, an input control, such as a foot pedal and/or button(s) present on the treatment component, can be used initiate a cycle which triggers each function of a given component in a given sequence (i.e., component 100, then component 102, and subsequently component 104). The cycle/sequence may be repeated at any suitable interval of time and for any suitable number of cycles as needed to remove the tattoo from the subject's dermis and surrounding tissue.

The application of electrical energy, plasma, mobilization fluid, and/or extraction (i.e., suction) through the one or more needle/probe-like structures present on the treatment end to the tattooed dermis and surrounding tissue can be controlled by a skilled/trained operator or technician with high precision. In preferred embodiments, the skilled/trained operator or technician can activate or deactivate the different functions of the system components individually or in combination using one or more input control unit(s), such as a foot pedal or button(s) present on the treatment component. In some embodiments, the operator/technician may apply electrical energy and depending on the extent to which the tattoo has been rendered undetectable, invisible, and/or non-discernible determine not to apply cold plasma, a mobilization fluid and actuate extraction. In certain other embodiments, the operator/technician may choose to further apply a mobilization fluid and extraction in order to further render the tattoo undetectable, invisible, and/or non-discernible. In yet another embodiment, the operator/technician may choose to only further apply extraction to remove dislodged and degraded tattoo ink particles, degradation by-products thereof, and/or tissue by-products thereof contained in bodily fluid without applying a mobilization fluid.

Electric Field Generating Component

Figure 7A:
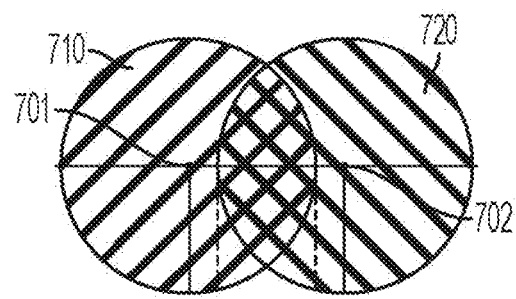
FIGS. 7A-7C illustrate the used of an array of electrodes that can be used in conjunction with F-CAP treatment. The electrodes can be separated from each other to achieve a generally uniform electric field strength over at least a portion of a target region by overlapping fields.
Figure 7B:
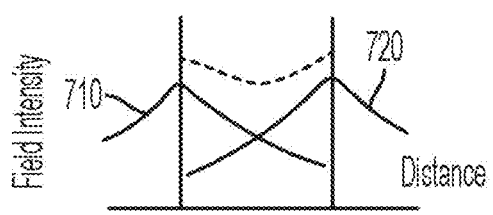
Figure 7C:
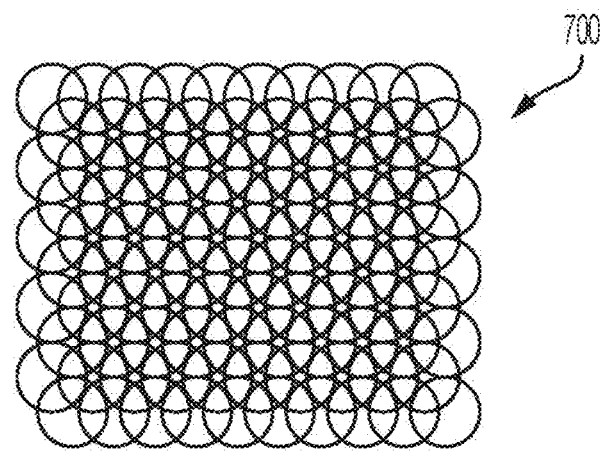

FIGS. 7A-7C illustrate the use of F-CAP together with an array of electrodes separated from each other to achieve a generally uniform electric field strength over at least a portion of a target region by overlapping fields. FIG. 7A illustrates two electrodes of such an array (701, 702) and their respective electric fields (710, 720)—and their region of overlap (730) when electrical energy is applied to the individual electrodes. FIG. 7B is a graph of electrical field intensity versus distance from each of electrodes 701 and 702 and further illustrating (by a dotted line) an increased field uniformity due to the overlapping fields. FIG. 7C illustrates a multi-electrode array 700 with electrodes in a "honeycomb" arrangement to further enhance field uniformity.

Alternative Embodiments

Figure 8:
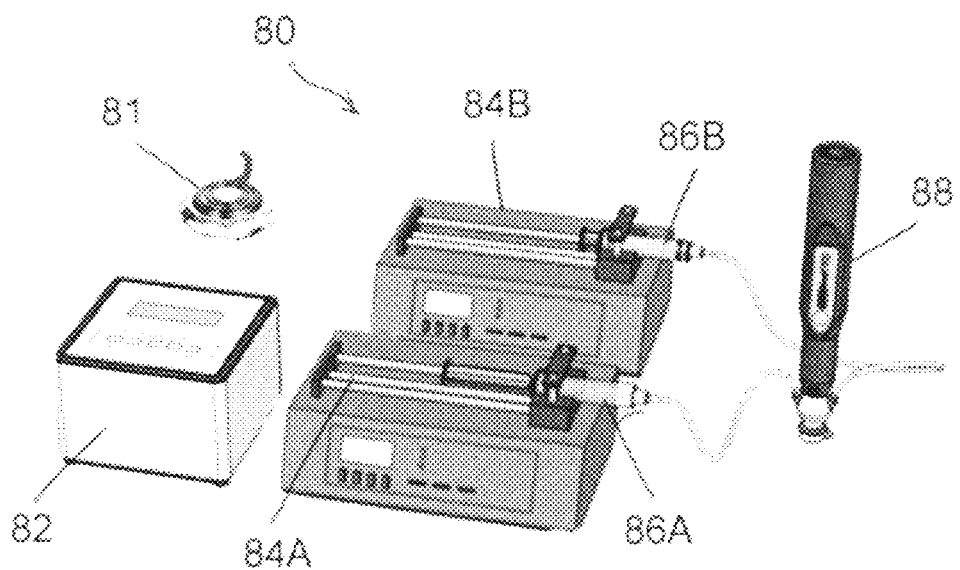
FIG. 8 shows another non-limiting example of a tattoo removal system capable of applying an activated liquid-gas mixture to a target tattoo region.

FIG. 8 illustrates another embodiment of the invention, in which a piezoelectric plasma generating system 80 includes controller 82, switch (foot petal) 81, syringe pumps 84A and 84B, syringes 86A and 86B and plasma delivery handpiece 88. The syringe pumps 84A and 84B can be used to deliver a pretreatment mobilization fluid to the target tattoo region as well as to deliver mobilization fluid during the application of plasma. For example, one syringe pump can deliver a liquid with entrained gas, e.g., water with dissolved carbon dioxide, such that the plasma generator can induce formation of an activated liquid gas mixture with plasma gas bubbles. One or both of the syringe pumps can also be activated in reverse to extract fluid with degraded tattoo particles following plasma treatment of the dermal region.

Figure 9:
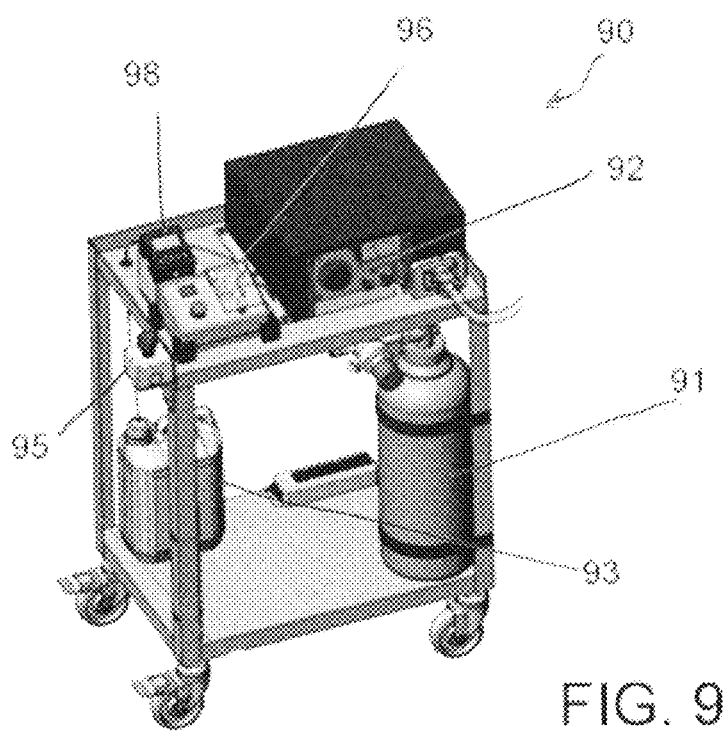
FIG. 9 shows yet another non-limiting example of a tattoo removal system capable of applying an activated liquid-gas mixture to a target tattoo region.

FIG. 9 illustrates yet another embodiment of the invention, in which a dielectric barrier plasma generating system 90 is shown including high voltage source 92, liquid pump 94, controller 96, display 98 and switch 95. They system 90 can further include a pressurized gas source 91 and a liquid source 93. In this system a gas, such as argon, neon, or other noble gas or air, can be delivered to a plasma generator as described above in FIG. 2 where the gas can ignited by the dielectric barrier electrode to create a plasma. The plasma can be mixed with liquid from the liquid source 93 in the plasma generator and then delivered as liquid entrained plasma gas bubbles to the target tattoo region.

Example 1

This example describes application of both cold atmospheric plasma (CAP) and fluid cold atmospheric plasma (F-CAP). The CAP treatment was delivered by electrically activating a gas (air) and injecting the resulting cold atmospheric plasma into a tattooed region of a rat. The F-CAP treatment involved forming plasma gas bubbles in a liquid (carbon dioxide infused water) and injecting this activated mixture into the same tattooed region.

This animal experiment followed IACUC protocols. The animal (six months old, weighing 880 grams) had been tattooed six-months previously using a violet-black tattoo ink (Millennium Mom's Ink) to form a linear tattoo to be treated and an adjacent control tattoo (dot shaped).

The CAP and F-CAP treatments were preceded by a pretreatment injection of a mobilization fluid. The mobilization fluid (distilled water) was first injected into the mouse's dermal target region of the tattoo. A 27 Gauge needle (Becton Dickson) and a 5 ml syringe were used to perform five pretreatment injections of the mobilization fluid in a pattern that spanned the length of the linear tattoo. Following the injections, five "blebs" were visible at the skin surface.

A piezoelectric-driven plasma generator with a distal needle injector was then used to apply the CAP. Fifteen lateral injections of the plasma (electrically activated air) were applied along the length of the tattoo.

Following the CAP treatment, external suction was applied using an Oiiwak dermatological vacuum applicator. Vacuum was applied 10 times across the CAP treated area for several seconds per each application.

The same animal then underwent a F-CAP treatment with the same piezoelectric plasma generator with a two needle delivery head. The fluid was carbon dioxide infused water. Electrical excitation of the this liquid-gas mixture induced plasma gas bubbles. Twenty injections were delivered.

Following Fluid-CAP, external suction was again performed using the Oiiwak dermatological vacuum applicator. Vacuum was applied five times across the CAP treated area for several minutes per each application.

The progress of the treatment was followed for a month. By day 32, there was a noticeable diminution in tattoo visibility and the skin had healed with no scarring. An untreated control dot of ink was clearly visible but the treated linear tattoo was essentially non-discernible. The animal was euthanized 6 weeks after treatment. Histology of the mouse's dermis revealed only rare ink particles could be found under microscopic investigation in the treated tattoo region.

Example 2

In this experiment, cold atmospheric plasma (CAP) formed by excitation of an inert gas (neon) was again followed by fluid-assisted cold atmospheric plasma (F-CAP). The plasma was induced in both treatments by a dielectric barrier discharge plasma generator. The F-CAP treatment, in this instance, involved electrically activating a mixture of neon gas and carbon-dioxide infused water and injecting the resulting fluid with entrained gas bubbles of cold atmospheric plasma into a tattooed region of a rat.

The animal experiment was again conducted according to IACUC protocols. The animal (mouse, approximated seven months old, weighing 1.2 kilograms) had been tattooed using a violet-black tattoo ink (Millennium Mom's Ink) six months earlier to form a linear tattoo and a control dot tattoo before the treatment.

The animal in this case was also pretreated with a mobilization fluid (distilled water), which was first injected into target region of the tattoo using a 30 Gauge needle and a syringe. Three injections of the mobilization fluid in a pattern that spanned the length of the linear tattoo. Following the injections, "blebs" were visible at the skin surface.

The CAP treatment involved 15 lateral injections of neon gas plasma with an exposure of several seconds per injection. The CAP treatment was directly followed by an F-CAP treatment.

For the F-CAP treatment, an activated liquid-gas mixture (Neon and carbon dioxide infused water) was injected via a dielectric barrier plasma generating handpiece attached to 23 Gauge needle. Fifteen lateral injections were delivered with a few seconds exposure dose per injection and estimated fluid injection of 15 milliliters.

Following this Fluid-CAP treatment, external suction was performs using the Oiiwak dermatological vacuum applicator. Vacuum was applied three times across the CAP treated area for 1 minutes per each application.

The progress of the treatment was again followed and there was a noticeable diminution in tattoo visibility and the skin had healed with no scarring.

Unless defined otherwise, all technical and scientific terms used herein have the same meanings as commonly understood by one of skill in the art to which the present teachings belong. All patents, patent applications and publications of any kind cited herein and the materials for which they are cited are specifically incorporated by reference in their entirety.

It should be understood that any method step or element described herein can be used in conjunction with any other method or element, respectively, whether or not such combination is described in a specific example or embodiment. All such permutations are embraced as part and parcel of the present invention.

Within this specification, embodiments have been described in a way that enables a clear and concise specification to be written, but it is intended and will be appreciated that embodiments may be variously combined or separated without departing from the invention. For example, it will be appreciated that all preferred features (element or method step) described and/or claimed are applicable to all aspects of the invention described herein. Every claimed feature should be deemed capable of multiple dependencies from other claimed features even if only one dependency is recited unless the combination of features is physically impossible.

Those skilled in the art will recognize, or be able to ascertain using no more than routine experimentation, many equivalents to the specific embodiments of the exemplary teachings described herein. Such equivalents are also intended to be encompassed by the following claims.

We claim:

1. A method of removing a tattoo from a subject's skin, comprising the steps of:
   subjecting at least one gas to an electrical field to create a cold plasma;
   delivering the cold plasma to tattoo ink particles within a target tattoo region of a tattooed dermis of the subject's skin;
   concurrently delivering a mobilization fluid to the target tattoo region;
   whereby the tattoo ink particles are dislodged by the delivery of said cold plasma and said mobilization fluid to the target tattoo region.

2. The method of claim 1 wherein the cold plasma and the mobilization fluid are delivered by a treatment component having an output end that delivers the cold plasma and the mobilization fluid to said tattooed dermis.

3. The method of claim 1, wherein the cold plasma comprises a cold atmospheric plasma.

4. The method of claim 1 wherein the cold plasma applies energy to the target tattoo region without raising a temperature of the target tattoo region more than about 1 degree C. to about 5 degrees C. above normal body temperature.

5. The method of claim 1, wherein the cold plasma further comprises at least one gas selected from air, carbon dioxide, oxygen, nitrogen, helium, argon, neon, xenon, and krypton.

6. The method of claim 1, wherein the mobilization fluid comprises at least one mobilization fluid selected from water, saline, and buffered aqueous solutions.

7. The method of claim 1, wherein the step of delivering the cold plasma to the tattoo ink particles within the target tattoo region further comprises accessing the target tattoo region via at least one hollow needle inserted into the subject's skin.

8. The method of claim 1 wherein the step of subjecting said at least one gas to the electrical field to create the cold plasma further comprises applying an alternating electric field having at least one frequency ranging from about 1 kHz to 100 MHz to said at least one gas.

9. The method of claim 8 wherein the step of applying said alternating electric field further comprises delivering an alternating current between about 0.1 and 10 microamperes to said at least one gas.

10. The method of claim 8 wherein the step of subjecting said at least one gas to the electrical field to create the cold plasma further comprises applying an alternating current between 1 and 10 microamperes to said at least one gas.

11. The method of claim 1 wherein the step of subjecting said at least one gas to the electrical field to create the cold plasma further comprises applying a voltage between 1 and 10 kV to said at least one gas.

12. The method of claim 8 wherein the step of subjecting said at least one gas to the electrical field to create the cold plasma further comprises applying a voltage between 4 and 6 kV to said at least one gas.

13. The method of claim 1, wherein the method further comprises extracting dislodged tattoo ink particles via suction of the mobilization fluid or a natural bodily fluid containing the dislodged tattoo ink particles from the target tattoo region.

14. A method of removing a tattoo from a subject's skin, comprising the steps of:
   forming an activated liquid-gas mixture comprising a liquid and at least one gas entrained as bubbles within the liquid, in which at least a portion of said at least one gas is in the form of a cold plasma; and
   delivering the activated liquid-gas mixture to a target tattoo region of a tattooed dermis of the subject's skin, whereby tattoo ink particles are dislodged by the delivery of the activated liquid-gas mixture to the target tattoo region.

15. The method of claim 14, wherein the step of forming the activated liquid-gas mixture further comprises applying the electric field to the liquid with entrained gas bubbles to induce cold plasma formation in the entrained gas bubbles and thereby activating the liquid-gas mixture.

16. The method of claim 14, wherein the step of forming the activated liquid-gas mixture further comprises applying a high energy electrical field to said at least one gas to form said cold plasma and then mixing the at least one gas with the liquid to form the activated liquid-gas mixture.

17. The method of claim 14, wherein the activated liquid-gas mixture is delivered by a treatment component having an output end that delivers the activated liquid-gas mixture to said tattooed dermis.

18. The method of claim 14, wherein the cold plasma comprises a cold atmospheric plasma.

19. The method of claim 14, wherein the cold plasma applies energy to the target tattoo region without raising a temperature of the target tattoo region more than 4 degrees C.

20. The method of claim 14, wherein the at least one gas in the activated liquid-gas mixture comprises at least one gas selected from air, carbon dioxide, oxygen, nitrogen, helium, argon, neon, xenon, and krypton.

21. The method of claim 14, wherein the liquid is selected from water, saline, and buffered aqueous solutions.

22. The method of claim 14, wherein the step of delivering the activated liquid-gas mixture to the target tattoo region further comprises accessing the target tattoo region via at least one hollow needle inserted into the subject's skin and delivering the activated liquid-gas mixture via said at least one hollow needle.

23. The method of claim 14, wherein the step of forming the activated liquid-gas mixture further comprises applying an alternating electric field having at least one frequency ranging from about 1 kHz to 100 MHz to said at least one gas.

24. The method of claim 23, wherein the step of applying said alternating electric field further comprises delivering an alternating current between about 0.1 and 10 microamperes to said at least one gas.

25. The method of claim 23, wherein the step of subjecting said at least one gas to said alternating electrical field to create the cold plasma further comprises applying an alternating current between 1 and 10 microamperes to said at least one gas.

26. The method of claim 23, wherein the step of subjecting said at least one gas to said alternating electrical field to create the cold plasma further comprises applying a voltage between 1 and 10 kV to said at least one gas.

27. The method of claim 23, wherein the step of subjecting said at least one gas to said alternating electrical field to create the cold plasma further comprises applying a voltage between 4 and 6 kV to said at least one gas.

28. The method of claim 14, wherein the method further comprises extracting the tattoo ink particles via suction of the mobilization fluid or natural bodily fluid containing the tattoo ink particles from the target tattoo region.

\* \* \* \* \*